(12) United States Patent
Bøe et al.

(10) Patent No.: US 9,700,622 B2
(45) Date of Patent: Jul. 11, 2017

(54) METHOD FOR INTRODUCING SIRNA INTO CELLS BY PHOTOCHEMICAL INTERNALISATION

(75) Inventors: Sigurd Bøe, Oslo (NO); Eivind Johannes Hovig, Oslo (NO)

(73) Assignee: PCI BIOTECH AS, Oclo (NO)

( * ) Notice: Subject to any disclaimer, the term of this patent is extended or adjusted under 35 U.S.C. 154(b) by 0 days.

(21) Appl. No.: 13/349,334

(22) Filed: Jan. 12, 2012

(65) Prior Publication Data

US 2012/0264807 A1 Oct. 18, 2012

Related U.S. Application Data

(63) Continuation of application No. 12/304,266, filed as application No. PCT/GB2007/002569 on Jul. 11, 2007, now abandoned.

(30) Foreign Application Priority Data

Jul. 11, 2006 (GB) .................................. 0613753.3

(51) Int. Cl.
| | |
|---|---|
| C07H 21/02 | (2006.01) |
| A61K 48/00 | (2006.01) |
| C12N 15/113 | (2010.01) |
| C12N 15/87 | (2006.01) |
| A61K 41/00 | (2006.01) |
| A61K 47/48 | (2006.01) |
| B82Y 5/00 | (2011.01) |
| C12N 15/11 | (2006.01) |

(52) U.S. Cl.
CPC .... *A61K 41/0071* (2013.01); *A61K 47/48969* (2013.01); *B82Y 5/00* (2013.01); *C12N 15/111* (2013.01); *C12N 15/113* (2013.01); *C12N 15/87* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,897,355 A | 1/1990 | Eppstein et al. | |
| 5,476,962 A | 12/1995 | Behr et al. | |
| 6,172,048 B1 | 1/2001 | Behr et al. | |
| 6,500,800 B1 | 12/2002 | Sobolev et al. | |
| 6,680,301 B2 | 1/2004 | Berg et al. | |
| 7,056,704 B2 | 6/2006 | Tuschl et al. | |
| 2004/0204377 A1* | 10/2004 | Rana ..................... | C12N 15/111 514/44 A |
| 2005/0008617 A1* | 1/2005 | Chen ..................... | A61K 9/5146 424/93.2 |
| 2006/0051405 A1 | 3/2006 | MacLachlan et al. | |

FOREIGN PATENT DOCUMENTS

| | | |
|---|---|---|
| GB | 0415263.3 | 7/2004 |
| WO | 96/07432 | 3/1996 |
| WO | 00/54802 | 9/2000 |
| WO | 02/44395 A1 | 6/2002 |
| WO | 02/44396 | 6/2002 |
| WO | 03/020309 | 3/2003 |
| WO | 2005/014837 A1 | 2/2005 |
| WO | 2006/003463 | 1/2006 |
| WO | 2008/007073 A3 | 1/2008 |

OTHER PUBLICATIONS

Hogset (Adv. Drug Del. Rev. 56:95-115, 2004).*
Kunath et al (Journal of Controlled Release 89 (2003) 113-125).*
Schiffelers et al (Expert Opin. Drug Deliv. (2006) 3(3):445-454).*
Aigner (Journal of Biomedicine and Biotechnology vol. 2006, Article ID 71659, pp. 1-15).*
Urban Klein et al (Gene Therapy (2005) 12, 461-466).*
Werth et al (Journal of Controlled Release 112 (2006) 257-270).*
Jorgensen et al (Nucleic Acid Therapeutics vol. 23, No. 2, 2013).*
Buchberger et al., "DOSPER Liposomal Transfection Reagent: A Reagent with Unique Transfection Properties," *Biochemica* 2:7-10, 1996.
Kukowska-Latallo et al., "Efficient transfer of genetic material into mammalian cells using Starburst polyamidoamine dendrimers," *Proc. Natl. Acad. Sci. USA* 93:4897-4902, May 1996.
Database Caplus on STN: Registry No. 168479-03-06, Entered STN: Oct. 6, 1995; Registry No. 181821-44-3, Entered STN: Oct. 10, 1996; Date of Search: Jun. 27, 2012, 3 pages.
Barthel et al., "Laboratory Methods—Gene Transfer Optimization with Lipospermine-Coated DNA," *DNA and Cell Biology* 12(6):553-560, 1993.
Behr et al., "Efficient gene transfer into mammalian primary endocrine cells with lipopolyamine-coated DNA," *Proc. Natl. Acad. Sci. USA* 86:6982-6986, 1989.
Chiu et al., "siRNA function in RNAi: A chemical modification analysis," *RNA* 9:1034-1048, 2003.
Czauderna et al., "Structural variations and stabilising modifications of synthetic siRNAs in mammalian cells," *Nucleic Acids Research* 31(11):2705-2716, 2003.
Geall et al., "Homologation of Polyamines in the Rapid Synthesis of Lipospermine Conjugates and Related Lipoplexes," *Tetrahedron* 56:2449-2460, 2000.
Høgset et al., "Photochemical internalization in drug and gene delivery," *Advanced Drug Delivery Reviews* 56:95-115, 2004.
McLaggan et al., "Pore forming polyalkylpyridinium salts from marine sponges versus synthetic lipofection systems: distinct tools for intracellular delivery of cDNA and siRNA," *BMC Biotechnology* 6:6, 12 pages, 2006.

(Continued)

*Primary Examiner* — Richard Schnizer
(74) *Attorney, Agent, or Firm* — Seed IP Law Group LLP

(57) ABSTRACT

The present invention relates to a method for introducing an siRNA molecule into the cytosol of a cell, said method comprising i) contacting said cell with an siRNA molecule, a carrier and a photosensitizing agent, and ii) irradiating the cell with light of a wavelength effective to activate the photosensitizing agent, wherein said carrier comprises a cationic polyamine such as a lipopolyamine in a non-liposomal formulation, polyethyleneimine (PEI), a betacyclodextrin amine polymer, an amine group containing dendrimer, and a cationic peptide. Cells or a population of cells obtainable by the method, a composition containing an siRNA molecule and the carrier molecule, kits and therapeutic uses of the above are also provided.

19 Claims, 18 Drawing Sheets

(56) References Cited

OTHER PUBLICATIONS

Figure 1:
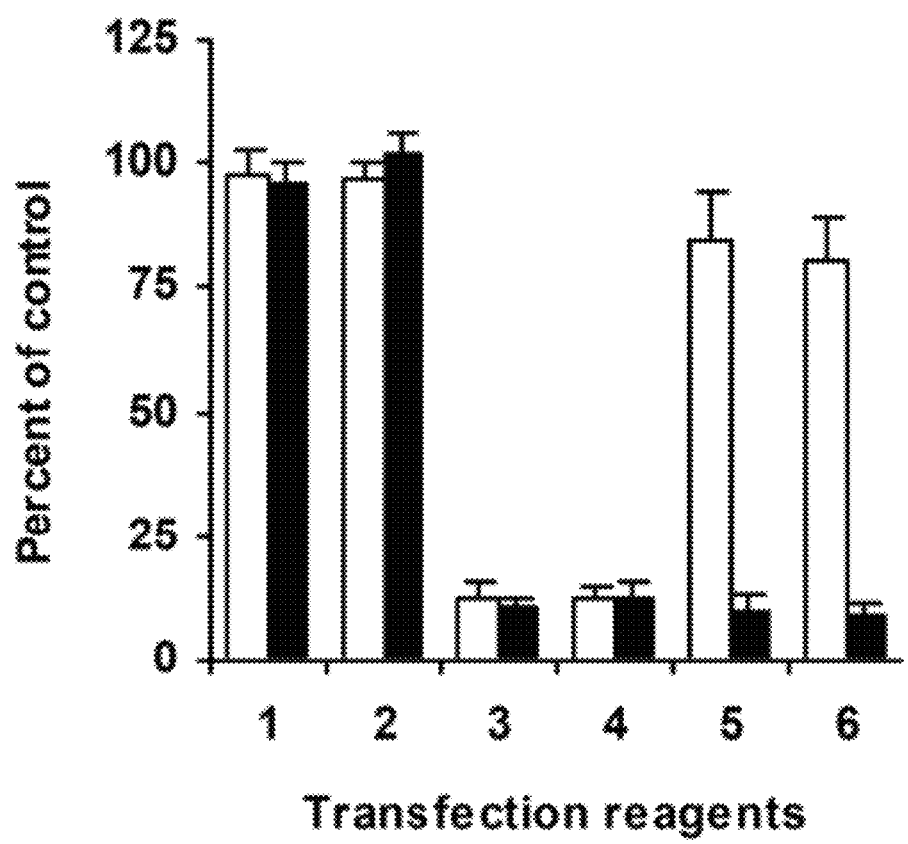

Pitard et al., Virus-sized self-assembling lamellar complexes between plasmid DNA and cationic micelles promote gene transfer, *Proc. Natl. Acad. Sci. USA* 94:14412-14417, 1997.
Remy et al., "Gene Transfer with a Series of Lipophilic DNA-Binding Molecules," *Bioconjugate Chem.* 5:647-654, 1994.
Verma et al., "Small Interfering RNAs Directed against β-Catenin Inhibit the in Vitro and in Vivo Growth of Colon Cancer Cells," *Clinical Cancer Research* 9:1291-1300, 2003.
Ahmed et al., "N4,N9-dioleoyl spermine is a novel nonviral lipopolyamine vector for plasmid DNA formulation," *Pharmaceutical Research* 22(6):972-980, 2005.
Berg et al., "Lysosomes and microtubules as targets for photochemotherapy of cancer," *J. Photochemistry and Photobiology* 65(3):403-409, 1997.
Boe et al., "Photochemically induced gene silencing using small interfering RNA molecules in combination with lipid carriers," *Oligonucleotides* 17(2):166-173, 2007.
Nishiyama et al., "Light-induced gene transfer from packaged DNA enveloped in a dendrimeric photosensitizer," *Nature Materials* 4(12):934-941, 2005.
Oliveira et al., "Photochemical internalization enhances silencing of epidermal growth factor receptor through improved endosomal escape of siRNA," *Biochimica et Biophysica Acta* 1768(5):1211-1217, 2007.
Spagnou et al., "Lipidic Carriers of siRNA: Differences in the formulation, cellular uptake, and delivery with plasmid DNA," *Biochemistry* 43(42):13348-13356, 2004.
Hassani et al., "Lipid-mediated siRNA delivery down-regulates exogenous gene expression in the mouse brain at picomolar levels," *The Journal of Gene Medicine* 7:198-207, 2005.
Ogris et al., "The size of DNA/transferrin-PEI complexes is an important factor for gene expression in cultured cells," *Gene Therapy* 5:1425-1433, 1998.
Scholz et al., "Therapeutic plasmid DNA versus siRNA delivery: Common and different tasks for synthetic carriers," *Journal of Controlled Release* 161:554-565, 2012.
Singha et al., "Polymers in Small-Interfering RNA Delivery," *Nucleic Acid Therapeutics* 21(3):133-147, 2011.
Boe et al., "Evaluation of Various Polyethylenimine Formulations for Light-Controlled Gene Silencing Using Small Interfering RNA Molecules," *Oligonucleotides* 18:123-132, 2008.
Podetz-Pedersen et al., "Gene Expression in Lung and Liver After Intravenous Infusion of Polyethylenimine Complexes of Sleeping Beauty Transposons," *Human Gene Therapy* 21:210-220, 2010.
Akhtar et al., "Nonviral delivery of synthetic siRNAs in vivo," *J. Clin. Invest.* 117:3623-3632, 2007.
Bøe et al., "Photochemically Induced Gene Silencing Using PNA-Peptide Conjugates," *Oligonucleotides* 16(2):145-157, 2006 (abstract only).
Chinese Office Action dated Sep. 9, 2010, corresponding to Chinese Patent Application No. 200780024620.7 (English translation), 14 pages.
Curiel, "Strategies to Adapt Adenoviral Vectors for Targeted Delivery," *Ann. New York Acad. Sci.* 886:158-171, 1999.
Drozdzik et al., "Antitumor effect of allogenic fibroblasts engineered to express Fas ligand (FasL)," *Gene Therapy* 5:1622-1630, 1998.
Du et al, "Generation of variable and fixed length siRNA from a novel siRNA expression vector," *Biochemical and Biophysical Research Communications* 345:99-105, 2006.
Elbashir et al., "Duplexes of 21-nucleotide RNAs mediate RNA interference in cultured mammalian cells," *Nature* 411:494-498, 2001.
Esfand et al., "Poly(amidoamine) (PAMAM) dendrimers: from biomimicry to drug delivery and biomedical applications," *DDT* 6(8):427-436, 2001.
Hannon et al., "Unlocking the potential of the human genome with RNA interference," *Nature* 431:371-378, 2004.
Høgset et al., "Photochemical Transfection: A New Technology for Light-Induced, Site-Directed Gene Delivery," *Human Gene Therapy* 11:869-880, 2000.
Hwang et al, "Effects of Structure of β-Cyclodextrin-Containing Polymers on Gene Delivery," Bioconjugate Chem. 12:280-290, 2001.
Jagla et al., "Sequence characteristics of functional siRNA," *RNA* 11:864-872, 2005.
Kang et al., *Foreign Medical Sciences (Blood Transfusion and Hematology)* 26(1):36-39, 2003.
Katoh et al., "Simple and rapid synthesis of siRNA derived from in vitro transcribed shRNA," *Nucleic Acids Research Supplement* No. 3:249-250, 2003.
Kichler et al , "Influence of Membrane-Active Peptides on Lipospermine/DNA Complex Mediated Gene Transfer," *Bioconjugate Chem.* 8:213-221, 1997.
Kulkarni et al., "Single Cell Kinetics of Intracellular, Nonviral, Nucleic Acid Delivery Vehicle Acidification and Trafficking," *Bioconjugate Chem.* 16:986-994, 2005.
Lage, "Potential applications of RNA interference technology in the treatment of cancer," *Future Oncology* 1(1):103-113, 2005.
Midoux et al., "Histidine Containing Peptides and Polypeptides as Nucleic Acid Vectors," *Somatic Cell and Molecular Genetics* 27(116):27-47, 2002.
Midoux et al., "Membrane Permeabilization and Efficient Gene Transfer by a Peptide Containing Several Histidines," *Bioconjugate Chem.* 9:260-267, 1998.
Minakuchi et al., "Atelocollagen-mediated synthetic small interfering RNA delivery for effective gene silencing in vitro and in vivo," *Nucleic Acids Research* 32(13), 2004, 7 pages.
Pan et al., "Antisense Applications for Biological Control," *Journal of Cellular Biochemistry* 98:14-35, 2006.
Peng et al., "Viral vector targeting," *Current Opinion in Biotechnology* 10:454-457, 1999.
Pichon et al., "Histidine-rich peptides and polymers for nucleic acids delivery," *Advanced Drug Delivery Reviews* 53:75-94, 2001.
Pon et al., "Large-scale synthesis of "Cpep" RNA monomers and their application in automated RNA synthesis," *Nucleosides, Nucleotides and Nucleic Acids* 24(5-7):777-781, 2005.
Pouton et al., "Polycation-DNA complexes for gene delivery: a comparison of the biopharmaceutical properties of cationic polypeptides and cationic lipids," *Journal of Controlled Release* 53:289-299, 1998.
Ramsay et al., "Polylysine and Polyornithine Gene Transfer Complexes: A Study of Complex Stability and Cellular Uptake as a Basis for their Differential in-vitro Transfection Efficiency," *Journal of Drug Targeting* 10(1):1-9, 2002.
Remy et al., "Gene transfer with lipospermines and polyethylenimines," *Advanced Drug Delivery Reviews* 30:85-95, 1998.
Selbo et al., "Photochemical Internalisation: A Novel Drug Delivery System," *Tumor Biol* 23:103-112, 2002.
Seyhan et al., "Complete, gene-specific siRNA libraries: Production and expression in mammalian cells," *RNA* 11:837-846, 2005.
Takasaki et al., "Selecting effective siRNA sequences based on the self-organizing map and statistical techniques," *Computational Biology and Chemistry* 30:169-178, 2006.
Wickham, "Targeting adenovirus," *Gene Therapy* 7:110-114, 2000.
Yoshida et al., "Development of gene therapy to target pancreatic cancer," *Cancer Sci* 95(4):283-289, 2004.
Yuan et al., "siRNA Selection Server: an automated siRNA oligonucleotide prediction server," *Nucleic Acids Research* 32:(Web Server Issue), W130-4, 5 pages.
Zhou et al., "PAMAM dendrimers for efficient siRNA delivery and potent gene silencing," *Chem. Comm.* 2362-2364, 2006.

\* cited by examiner

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial sequence
<220> FEATURE:
<223> OTHER INFORMATION: Primer

<400> SEQUENCE: 1
aagttcaagc tcaacaagtc agaac                                          25

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
catctgtcct tttccccaag a                                              21

<210> SEQ ID NO 3
<211> LENGTH: 18
<212> TYPE: DNA
<213> ORGANISM: Artificial sequence
<220> FEATURE:
<223> OTHER INFORMATION: Primer
```

<400> SEQUENCE: 3
gcccgaaacg ccgaatat                                                        18

<210> SEQ ID NO 4
<211> LENGTH: 22
<212> TYPE: DNA
<213> ORGANISM: Artificial sequence
<220> FEATURE:
<223> OTHER INFORMATION: Primer

<400> SEQUENCE: 4
cgtggctctc ttatcctcat ga                                                   22

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
cgctgctgaa catgctcaac                                                      20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tcgaacacct gctggatgac                                                      20

<210> SEQ ID NO 7
<211> LENGTH: 19
<212> TYPE: RNA
<213> ORGANISM: Artificial sequence
<220> FEATURE:
<223> OTHER INFORMATION: siRNA first strand

<400> SEQUENCE: 7
ugagcaaguu caauaaaga                                                       19

<210> SEQ ID NO 8
<211> LENGTH: 19
<212> TYPE: RNA
<213> ORGANISM: Artificial sequence
<220> FEATURE:
<223> OTHER INFORMATION: siRNA second strand

<400> SEQUENCE: 8
ucuuuauuga acuugcuca                                                       19

<210> SEQ ID NO 9
<211> LENGTH: 19
<212> TYPE: RNA
<213> ORGANISM: Artificial sequence
<220> FEATURE:
<223> OTHER INFORMATION: Control siRNA first strand

<400> SEQUENCE: 9
cgcauaagug aaauagaau                                                       19

<210> SEQ ID NO 10

```
<211> LENGTH: 19
<212> TYPE: RNA
<213> ORGANISM: Artificial sequence
<220> FEATURE:
<223> OTHER INFORMATION: Control siRNA second strand

<400> SEQUENCE: 10
auucuauuuc acuuaugcg                                                    19
```

METHOD FOR INTRODUCING SIRNA INTO CELLS BY PHOTOCHEMICAL INTERNALISATION

CROSS-REFERENCE TO RELATED APPLICATIONS

This application is a continuation of U.S. patent application Ser. No. 12/304,266, filed May 11, 2009 now abandoned; which is a national stage application filed under 35 U.S.C. §371 of International Patent Application No. PCT/GB2007/002569 accorded an international filing date of Jul. 11, 2007, which claims the benefit of priority to United Kingdom (GB) Patent Application Serial No. 0613753.3, filed Jul. 11, 2006. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 900162_402D1_SEQUENCE_LISTING_ST25.txt. The text file is 2 KB, was created on Jun. 27, 2012, and is being submitted electronically via EFS-Web.

The present invention relates to a method for introducing short interfering RNA (siRNA) into cells, preferably into the cytosol of cells, using a photosensitising agent and a carrier molecule and irradiation of the cells with light of a wavelength effective to activate the photosensitising agent, and to the use of this method for altering gene activity, e.g. gene silencing in vitro or in vivo.

The process of RNA interference occurs in many organisms and in this process, double-stranded non-coding RNA silences gene expression in a sequence specific, post-transcriptional manner. In nature, the phenomenon protects an organism's genome from foreign, invading nucleic acids such as transposons, transgenes and viral genes.

The introduction of double-stranded RNA (dsRNA) into a cell triggers this process of RNA silencing, and any mRNA in the cell corresponding in sequence to the introduced dsRNA is degraded. RNA silencing pathways involve the conversion of dsRNA into short interfering RNAs (siRNAs) that direct ribonucleases to homologous mRNA targets. The enzyme Dicer processes the dsRNA into siRNAs, which are in general 20-25 nucleotides long. The siRNAs then assemble into endoribonuclease-containing complexes known as RNA-induced silencing complexes (RISCs), which are guided to complementary RNA molecules, where they cleave and destroy the target mRNA. Small amounts of dsRNA can silence a large amount of target mRNA due to an amplification component of RNA silencing (reviewed in Hannon and Rossi (2004), Nature 431, 371-378).

Knowledge that siRNA molecules are key components of the pathway led to the testing of chemically synthesised siRNA molecules of approximately 20 to 22 base pairs in length, corresponding to targeted RNA or DNA sequences. These molecules were shown to act to disrupt the expression of the targeted sequences in mammalian cells (Elbashir S. M. et al., (2001) Nature 411, 494-498). A 20-nucleotide siRNA is usually sufficiently long to induce gene-specific silencing, but sufficiently short to evade a host response. The decrease in expression of targeted gene products can be extensive with 90% silencing induced by a few molecules of siRNA.

siRNA technology has thus been developed as a general technique for sequence specific gene silencing. Gene silencing has many applications, both in vitro and in vivo, as both a research tool and a therapeutic strategy. The high potency and specificity that is seen when siRNA technology is used makes this technology particularly attractive.

In all cases, delivery of the siRNA molecules to the cells represents a major challenge, as for gene silencing to occur, it is necessary for the siRNA molecules to enter the cells in sufficient concentrations to be useful. The strength of the silencing response and its duration is affected by the amount of siRNA that is delivered to the cell, and it has been shown that by supplying the siRNA in sufficiently high concentrations, even a relatively weak siRNA molecule can silence its target. This should however be balanced against the fact that it is known that administering large amounts of siRNA into a cell can lead to undesired effects such as "off target" effects (i.e. unwanted changes in protein expression levels) or the activation of innate immune pathways.

In general, siRNA has been applied to cells by using standard transfection protocols for nucleic acids, such as by using liposomes, cationic lipids, anionic lipids, and microinjection. siRNA is a double stranded molecule and as such, delivery and cellular uptake of the molecule is more difficult than for antisense, which binds to serum proteins to be taken up by cells. Various different strategies have been used, and commercially available kits exist for this purpose. As noted above, efficient transfection is highly desirable since the potency of gene silencing is at least in part dependent on the concentration of siRNA in the cell, but administration to cells in high concentrations may also cause undesirable side effects.

Administration at high levels also often requires high concentrations of transfection reagents, and this can have adverse effects on the cells including reduced cell viability and various other side effects, both phenotypic and non-phenotypic. Furthermore, when high concentrations of reagents are used, specific delivery is not achieved.

Targeted delivery of nucleic acid molecules such as siRNA is also, in general, not reliable enough. Viruses could be used for this purpose, however, there are safety concerns with this approach and systemic viral delivery is difficult to achieve.

siRNA acts in the cytosol of cells, and it is necessary for the molecule to reach the cytosol for it to act. In view of the above considerations, it would be desirable to develop an improved method of delivering siRNA to the cytosol of a cell. Desirable properties of such an improved method include i) the ability to generate time and site specific delivery of siRNA molecules to its site of action, ii) the avoidance of the use of high concentrations of transfection reagent and/or siRNA and/or iii) enhanced siRNA silencing in cell lines. In particular, such methods would reduce the overall number of siRNA:lipid complexes required to achieve a certain level of gene silencing or improve on it. In such methods the siRNA:transfection reagent ratio may be altered whilst maintaining a certain amount of gene silencing or improving on it. Increasing the siRNA:lipid ratio is useful since it would minimize the inhibitor effects that are observed when using high concentrations of transfection reagents.

The overall aim of the improved method can alternatively be stated as a desire to balance the need for effective and controllable siRNA delivery to the cytosol with reduction of adverse side effects caused by either high concentrations of transfection reagents, or non-specific effects, e.g. in particular cell types. As noted above, the reduction of the overall number of siRNA:lipid complexes and/or an increase in the siRNA:lipid ratio would contribute to this goal.

In order to achieve these goals, the inventors have combined the use of a carrier (transfection reagent) with the technique of photochemical internalisation (PCI). The particular carrier that is chosen delivers the siRNA molecule to intracellular compartments of the cell, e.g. endocytic vesicles such as the endosome and/or the lysosome of the cell. Alternative intracellular compartments into which the siRNA:lipid complex may be taken up include the Golgi apparatus and the endoplasmic reticulum.

Release of the siRNA molecule from the intracellular vesicle occurs as a consequence of the PCI technique. This is dependent on exposure of the cell to a photosensitising compound and subsequent irradiation, and it can be seen that the release of the siRNA molecule only occurs following irradiation of the cell and as such, this release into the cytosol where its effects, are mediated can be controlled in a spatial or temporal manner. Only cells which i) contain siRNA in their intracellular vesicles, have been exposed to the photochemical internaliser and iii) are exposed to irradiation, will release the siRNA molecule into the cytosol of the cell for it to act on mRNA in that cell.

In general, transfection reagents need to be used at high concentrations to optimise the delivery of siRNA to the cytosol. The inventors have surprisingly observed that by using low concentrations of transfection reagents (and a photochemical internaliser), the transfection step can be used to direct the siRNA to intracellular vesicles, such as the endosome, where it is contained until its release is triggered by the application of irradiation. The method thus allows siRNA to reach its site of action without the need to use high concentrations of transfection reagent or siRNA. Furthermore, the timing and location of the release of the siRNA molecule from intracellular vesicles such as the endosome can be controlled by using the PCI technique.

Thus, in a first aspect, the invention provides a method for introducing an siRNA molecule into the cytosol of a cell, comprising contacting said cell with an siRNA molecule, a carrier and a photosensitising agent, and irradiating the cell with light of a wavelength effective to activate the photosensitising agent. Once activated, intracellular compartments within said cell containing said photosensitising agent release siRNA contained in these compartments into the cytosol.

PCI is a technique which uses a photosensitising agent, in combination with an irradiation step to activate that agent, and achieves release of molecules co-administered to the cell into the cell's cytosol. This technique allows molecules that are taken up by the cell into organelles, such as endosomes, to be released from these organelles into the cytosol, following irradiation.

The basic method of photochemical internalisation (PCI), is described in WO 96/07432 and WO 00/54802, which are incorporated herein by reference. As set out above, the molecule to be internalised (which for use according to the present invention would be the siRNA molecule), in this case with a carrier molecule, and a photosensitising agent are brought into contact with a cell. The photosensitising agent, carrier molecule and the molecule to be internalised are taken up into a cellular membrane-bound subcompartment within the cell. On exposure of the cell to light of the appropriate wavelength, the photosensitizing agent is activated which directly or indirectly generates reactive species which disrupt the intracellular compartment membranes. This allows the internalized molecule to be released into the cytosol.

These methods use the photochemical effect as a mechanism for introducing otherwise membrane-impermeable (or poorly permeable) molecules into the cytosol of a cell in a manner which does not result in widespread cell destruction or cell death if the methodology is suitably adjusted to avoid excessive toxic species production, e.g. by lowering illumination times or photosensitizer dose.

This method is particularly advantageous for introducing siRNA into cells because it allows the use of lower concentrations of carrier or transfection reagent and/or siRNA than is required for conventional siRNA transfection, whilst achieving effective gene inhibition. Furthermore, the timing and location of irradiation to release the siRNA molecule may be controlled such that it is released only at the time and location that is desired to achieve the required effects. As such, exposure of cells to siRNA and carrier is minimised, and undesirable side effects are minimised. This is in contrast to the standard techniques for introducing siRNA into cells, where it is not possible to control the timing and location of the release of siRNA and high concentrations of transfection reagent are needed. By lowering the carrier amount (changing the siRNA:carrier ratio) compared to the amount that is advocated for use or by lowering the overall number of siRNA:carrier complexes that are applied to the cell it may also be possible to minimise the siRNA leakage from the intracellular compartments prior to PCI irradiation.

It has further been shown that by using the carriers as defined herein with PCI to deliver siRNA, strong gene silencing effects can be achieved without also causing cytotoxicity. For example, using PEI (Mw 25000) at 1 µg/ml with 100 nM siRNA and light doses of up to 40 seconds, no cytotoxic effects were observed (see FIG. 11B). Under these conditions, strong gene silencing effects were observed (see FIG. 10).

RNA is a polymer of ribonucleotides, each containing the sugar ribose in association with a phosphate group and a nitrogenous base (typically, adenine, guanine, cytosine, or uracil). As is the case for DNA, RNA can form complementary hydrogen bonds, and RNA may be double-stranded (dsRNA), single-stranded (ssRNA) or double-stranded with a single-stranded overhang. "Small interfering RNA" (siRNA) refers to double-stranded RNA molecules from about 10 to about 30 nucleotides long that specifically interfere with protein expression by binding to mRNA molecules. Preferably, siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27, 28 or 29 nucleotides in length.

The length of one strand designates the length of an siRNA molecule. For instance, an siRNA that is described as 21 ribonucleotides long (a 21-mer) could comprise two opposite strands of RNA that anneal together for 19 contiguous base pairings. The two remaining ribonucleotides on each strand would form an overhang. When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

siRNAs that comprise an overhang are desirable. The overhang may be at the 5' or the 3' end of a strand. Preferably, it is at the 3' end of the RNA strand. The length of an overhang may vary, but preferably is about 1 to about 5 nucleotides, and more preferably is about 2 nucleotides long. Preferably, the siRNA of the present invention will comprise a 3' overhang of about 2 to 4 nucleotides. More preferably, the 3' overhang is 2 ribonucleotides long. Even more preferably, the 2 ribonucleotides comprising the 3' overhang carry uracil (U) bases.

siRNAs are designed to interact with a target ribonucleotide sequence, in other words they complement a target sequence so as to bind to the target sequence, i.e. one strand of the siRNA is complementary to a region of the target sequence.

siRNA molecules having modified backbones so as to increase their half life have also been generated (e.g. as described in Chiu et al., (2003), RNA. 9(9), 1034-48 and Czauderna et al., (2003), Nucleic Acids Research 31, 2705-2716). The term "siRNA" thus also includes such modified molecules. Reference to siRNA thus encompasses derivatives or variants of siRNA which exhibit the same function, i.e. interaction with a target mRNA sequence. Preferred variants include those in which a modified backbone has been used (as above) or one or more non-naturally occurring bases is used.

The method may be used to introduce more than one type of siRNA molecule into a cell: In other words, siRNA molecules having different sequences can be introduced simultaneously into a cell. If multiple siRNA molecules are to be introduced, this can be achieved by simultaneously associating more than one siRNA molecule with the carrier. Alternatively, each type of siRNA molecule can separately be associated with a carrier.

There are several methods for preparing siRNAs, such as chemical synthesis, in vitro transcription, siRNA expression vectors, and PCR expression cassettes. Such techniques are well known in the art. See for example Pon et al., (2005) Nucleosides Nucleotides Nucleic Acids. 24(5-7): 777-81, Du et al., (2006), Biochem. Biophys. Res. Commun. 345 (1):99-105 and Katoh et al., (2003), Nucleic Acids Res Suppl. (3): 249-50.

Similarly, methods for designing siRNA molecules so as to achieve the desired outcome have been well documented. The siRNA target site must first be chosen. This can be carried out by using various techniques (see e.g. Jagla et al., (2005); RNA. 11(6):864-72 and Takasaki et al., (2006), Comput. Biol. Chem. 30(3): 169-78).

The method of the invention achieves translocation of the siRNA molecule into the cytosol. It will be appreciated however that uptake of each and every molecule contacted with the cell is not achievable. Significant and improved uptake relative to background levels in which no PCI or carrier is used is however achievable.

Preferably methods of the invention allow the uptake of siRNA molecules at sufficient levels that their effect is evident in the expressed products of those cells. The appropriate concentration of siRNA to be contacted with the cell may be adjusted to achieve this aim, e.g. to achieve a reduction in expression of a target gene of at least 10%, e.g. at least 20, 30, 40 50, 60, 70, 80 or 90% reduction (e.g. in the expression of one or more proteins encoded by the target gene) after incubation with cells for e.g. 24, 48, 72 or 96 hours (e.g. 24 to 48 hours). Similarly, the carrier type and/or concentration, the photosensitising agent type and/or concentration and the irradiation time can be adjusted to achieve the reduction set out above.

This can be measured by determining the level of protein in the cell, using standard techniques known in the art such as Western Blotting. The level of reduction of the protein is dependent on the half-life of the protein, i.e. pre-existing protein will be removed in accordance with its half-life. Thus a reduction in expression of at least 10, 20, 30, 40, 50, 60, 70, 80 or 90% is achieved relative to expression at the same time point without siRNA so that half-life is taken into account.

This can alternatively be measured in terms of the effect of the siRNA molecule on the amount of mRNA that is present in the cell, e.g. the method can be carried out to achieve a reduction in mRNA levels of at least 10%, e.g. at least 20, 30, 40, 50, 60, 70, 80 or 90% reduction after incubation with cells for e.g. 24, 48, 72 or 96 hours e.g. 24 to 48 hours) relative to mRNA levels of the target sequence at the same time point without siRNA. This can also be measured using standard techniques known in the art such as hybridisation or blotting techniques and RT-PCR.

Since the present methods require the use of significantly less carrier or transfection agent (and/or less siRNA, depending on whether the overall number of complexes is to be reduced, or the siRNA:carrier or transfection agent ratio is to be modified, or both) than standard methods for transfecting siRNA molecules, it is also possible to express the improvement in transfection using the method of the invention in terms of the amount of carrier or transfection agent that is required to achieve a certain amount of reduction in protein expression or mRNA levels. For example, the method of the invention preferably allows a certain reduction in target protein expression or mRNA levels (e.g. of at least 10%, e.g. at least 20, 30, 40, 50, 60, 70, 80 or 90% as described above) using a carrier concentration and/or siRNA concentration that is e.g. at least 10, 20, 30, 40, 50 or 60% lower than the amount of carrier that is required to achieve the same level of reduction in target protein expression or mRNA levels without PCI.

Comparisons can also be made between the levels of reduction, in protein expression or mRNA levels that are seen at a certain siRNA and carrier concentration, in the presence and absence of PCI. For example, the method of the invention preferably allows a reduction in target protein expression or mRNA levels of at least 10%, e.g. at least 20, 30, 40; 50, 60, 70, 80 or 90%, as described above, compared to protein expression or mRNA levels achieved by carrying out the method in the absence of the irradiation step of the PCI technique.

The term "cell" is used herein to include all eukaryotic cells (including insect cells and fungal cells). Representative "cells" thus include all types of mammalian and non-mammalian animal cells, plant cells, insect cells, fungal cells and protozoa. Preferably however the cells are mammalian, for example cells from cats, dogs, horses, donkeys, sheep, pigs, goats, cows, mice, rats, rabbits, guinea pigs, but most preferably from humans.

As used herein "contacting" refers to bringing the cells and the photosensitizing agent and/or siRNA and carrier into physical contact with one another under conditions appropriate for internalization into the cells, e.g. preferably at 37° C. in an appropriate nutritional medium, e.g. from 25-39° C.

The photosensitising agent is an agent which is activated on illumination at an appropriate wavelength and intensity to generate an activated species. Conveniently such an agent may be one which localises to intracellular compartments, particularly endosomes or lysosomes. A range of such photosensitising agents are known in the art and are described in the literature, including in WO96/07432, which is incorporated herein by reference. Mention may be made in this respect of di- and tetrasulfonated aluminium phthalocyanine (e.g. $AlPcS_{2a}$), sulfonated tetraphenylporphines ($TPPS_n$), nile blue, chlorin $e_6$ derivatives, uroporphyrin I, phylloerythrin, hematoporphyrin and methylene blue which have been shown to locate in endosomes and lysosomes of cells in culture. This is in most cases due to endocytic uptake of the photosensitizer. Thus, the photosensitizing agent is preferably an agent which is taken up into the internal compartments of the cell, e.g. lysosomes and/or endosomes. Further appropriate photosensitizers for use in the invention are described in WO03/020309, which is also incorporated herein by reference, namely sulphonated meso-tetraphenyl chlorins, preferably $TPCS_{2a}$.

However, other photosensitizing agents which locate to other intracellular compartments for example the endoplasmic reticulum or the Golgi apparatus may also be used. It is also conceivable that mechanisms may be at work in which the effects of the photochemical treatment are on other components of the cell (i.e. components other than membrane-restricted i.e. membrane enclosed compartments). Thus, for example one possibility may be that the photochemical treatment destroys molecules important for intracellular transport or vesicle fusion. Such molecules may not necessarily be located in membrane-restricted compartments, but the photochemical damage of such molecules may nevertheless lead to photochemical internalisation of the carrier:siRNA complexes, e.g. by a mechanism in which photochemical effects on such molecules leads to reduced transport of the molecule to be internalized (i.e. the siRNA molecule) to degradative vesicles such as lysosomes, so that the molecule to be internalized can escape to the cytosol before being degraded.

Examples of molecules not necessarily located in membrane restricted compartments are several molecules of the microtubular transport system such as dynein and components of dynactin; and for example rab5, rab7, N-ethylmaleimde sensitive factor (NSF), soluble NSF attachment protein (SNAP) and so on.

Classes of suitable photosensitising agents which may be mentioned thus include porphyrins, phthalocyanines, purpurins, chlorins, (particularly chlorin derivatives of the prophyrins described below) benzoporphyrins, lysomotropic weak bases, naphthalocyanines, cationic dyes and tetracyclines or derivatives thereof (Berg et al., (1997), J. Photochemistry and Photobiology, 65, 403-409). Other suitable photosensitising agents include texaphyrins, pheophorbides, porphycenes, bacteriochlorins, ketochlorins, hematoporphyrin derivatives, and derivatives thereof, endogenous photosensitizers induced by 5-aminolevulinic acid and derivatives thereof, dimers or other conjugates between photosensitizers.

Preferred photosensitising agents include $TPPS_4$, $TPPS_{2a}$, $AlPcS_{2a}$, $TPCS_{2a}$ and other amphiphilic photosensitizers. Other suitable photosensitizing agents include the compound 5-aminolevulinic acid or esters of 5-aminolevulinic acids or pharmaceutically acceptable salts thereof.

"Irradiation" of the cell to activate the photosensitising agent refers to the administration of light directly or indirectly as described hereinafter. Thus cells may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells.

In this method, the siRNA molecule to be introduced into the cell is attached to or associated with or conjugated to one or more carrier molecules or transfection agents which act to facilitate or increase the uptake of the photosensitizing agent or the siRNA molecule into the cell. This attachment, association or conjugation may be performed prior to contacting the siRNA molecule and its carrier with the cell or at the time of said contact by virtue of bringing these molecules into contact.

The terms carrier and transfection agent are used interchangeably herein.

The carrier molecule may be associated, bound or conjugated to the siRNA molecule or to both the siRNA and the photosensitizing agent. Thus, for example the siRNA may be attached to the carrier via charge:charge interactions. As mentioned above, more than one carrier may be used simultaneously, and the carrier may be associated, bound or conjugated to more than one siRNA molecule, or more than one type of siRNA molecule.

Preferably the carrier comprises a compound, preferably in a non-liposomal formulation that contains two or more amine groups i.e. is a polyamine and which is cationic and preferably protonatable (i.e. may be protonated to carry one or more additional hydrogen atoms under suitable reaction conditions) at different pH values. The different pH values applies to different values for protonatable atoms within a single molecules and/or within different molecules.

The term "protonatable" is used herein to mean that a group is capable of accepting a hydrogen atom, i.e. a protonatable group is a hydrogen accepting group. It is clear that the ability of a group to accept hydrogen depends not only on the nature of the group, but also on the pH to which the group is exposed. Preferably said protonatable group contains a nitrogen atom and it is this atom which accepts the hydrogen atom.

As referred to herein, "cationic" denotes that the overall, or net, charge of the molecule is +1 pr higher. This is preferably measured at physiological pH, i.e. pH 7.2. The molecule may have a higher charge, e.g. +2 or higher, +3 or higher, +4 or higher, +5 or higher, +6 or higher, +7 or higher, +8 or higher, +9 or higher, +10 or higher, +11 or higher, +12 or higher, +13 or higher, +14 or higher, +15 or higher, +20 or higher, +25 or higher, +50 or higher, +75 or higher, +100 or higher, +150 or higher, +200 or higher, +250 or higher, +300 or higher, +400 or higher, +500 or higher, +750 or higher or +1000 or higher.

Cationic polyamines for use in accordance with methods of the invention are as defined hereinafter and include (a) a lipopolyamine in a non-liposomal formulation, (b) polyethyleneimine (PEI) having an $M_n$ value of 500-20000 by GPC, (c) a betacyclodextrin amine polymer of formula

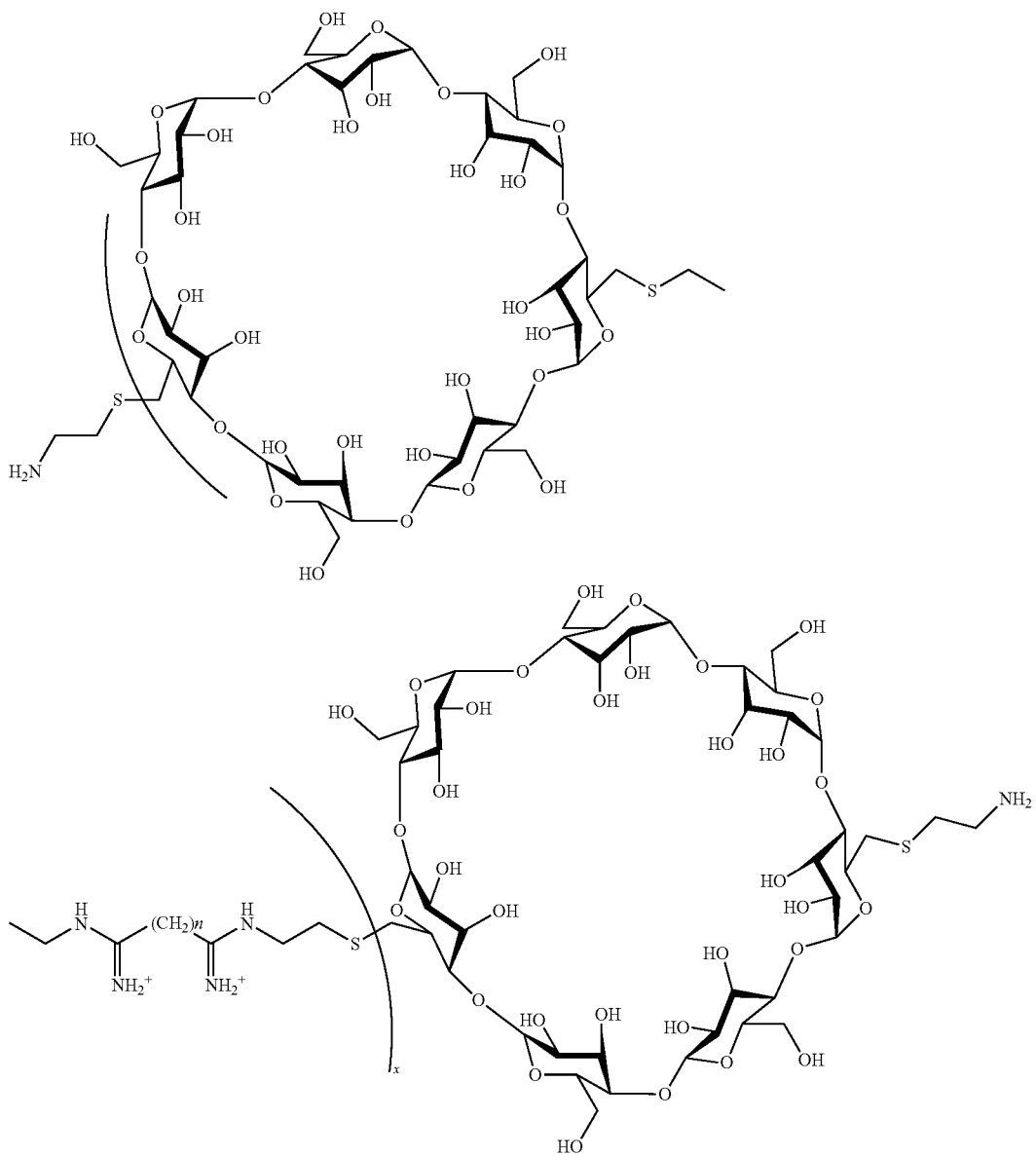

wherein X is an integer from 1 to 100 inclusive and n is an integer from 4 to 10 inclusive, (d) an amine group containing dendrimer, and
(e) a cationic peptide.

Preferably, the polyamine as referred to herein contains primary or secondary amine groups, or a mixture thereof (e.g. at least two primary amine groups). Preferably, the polyamine region has at least 2, 3, 4; 5 or 6 nitrogen atoms and a charge of at least +1, +2, +3, +4, or +5 (or at least +6, +7, +8, +9, +10, +11, +12, +13, +14, +15, +20, +25, +50, +75, +100, +150, +200, +250, +300, +400, +500, +750 or +1000) at physiological pH, e.g. some or all of the amine groups are charged. Preferably at least one (e.g. at least 2, 3 or 4) nitrogen containing group e.g. NH is uncharged at physiological pH. The pKa at which the last amine of the polyamine is protonated, e.g. the lipopolyamine is preferably approximately 5.5, i.e. on decreasing the pH, or adding acidic compounds, the last amine to be protonated is protonated at a pH less than or equal to 5.5.

In one embodiment the carrier comprises a lipopolyamine in a non-liposomal formulation. By lipopolyamine it is meant an amphiphilic molecule comprising at least one hydrophilic polyamine region (i.e. which contains two or more amine groups) and one lipophilic region. The lipophilic region may contain one or more lipophilic chains.

The polyamine region of the lipopolyamine preferably has the formula (I)

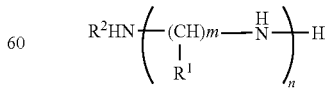

in which m is an integer greater than or equal to 2 and n is an integer greater than or equal to 1, it being possible for m to vary between the different carbon groups included between two amines, i.e. each $(CH)_m$—NH group may have a different m value, and m may be the same or different where it appears in said formula. At each position $R^1$ is a hydrogen or a linking group to the lipo portion of the lipopolyamine or the lipo portion itself as described hereinafter, and may be the same of different at each carbon atom. $R^2$ is a hydrogen or a linking group to the lipo portion of the lipopolyamine or the lipo portion itself as described hereinafter. Preferentially, m is between 2 and 6 inclusive, more preferably 3 or 4 and n is between 1 and 5 inclusive, more preferably 3.

Preferably only one of $R^1$ and $R^2$ is a linker, a linker attached to the lipo portion of the polyamine, or the lipo portion of the polyamine. Preferably only one $R^1$ group is a linker, the linker attached to the lipo portion of the polyamine or the lipo portion of the polyamine. $R^2$ is preferably H.

When $R^1$ or $R^2$ is the lipo portion itself or is a linker which is attached to the lipo portion of the polyamine, formula (I) is the lipopolyamine. Thus formula (I) is the polyamine region only when $R^1$ or $R^2$ is not the lipo portion or a linking group to which a lipo portion is attached.

Still more preferentially, the polyamine region is represented by the following formula

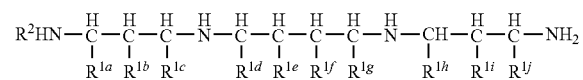

Wherein $R^2$ and $R^{1a}$ to $R^{1j}$ are as $R^1$ defined above, and preferably $R^{1a}$ is a linker and the remaining $R^1$ groups and $R^2$ are hydrogen.

The linking group is comprised of bonds that are stable under normal conditions.

Preferably $R^1$ or $R^2$ represents a hydrogen atom or a radical of general formula II:

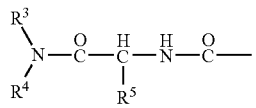

in which $R^3$ and $R^4$, which may be identical or different, each represent a saturated aliphatic radical $C_pH_{2p+2}$ or unsaturated aliphatic radical $C_9H_{2p}$ or $C_pH_{2p-2}$, p being an integer between 12 and 22 inclusive, and $R^5$ represents a hydrogen atom or an alkyl radical containing 1 to 4 carbon atoms optionally substituted with a phenyl radical.

Alternatively, $R^1$ or $R^2$ may each be a radical of general formula III:

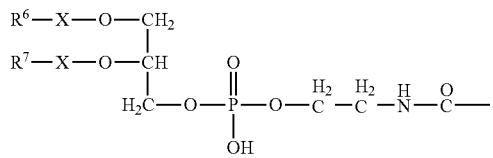

in which X represents a methylene group (—$CH_2$—) or a carbonyl group (—CO—), and $R^6$ and $R^7$, which may be identical or different, each represent a saturated aliphatic radical $C_{p'}H_{2p'+2}$ or unsaturated aliphatic radical $C_{p'}H_{2p'}$ or $C_{p'}H_{2p'-2}$, p' being an integer between 11 and 21 inclusive.

Irrespective of the values of m and n, only one of the symbols $R^1$ and $R^2$ can represent a radical of general formula (II) or (III), When n is between 2 and 5, the values of m in the different fragments

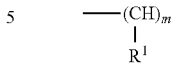

may be identical or different.

In a preferred embodiment of formula (I) n is equal to 3 and the values of m in the fragments

are identical or different and represent 3 or 4, and either $R^1$ or $R^2$ represents: either a radical of general formula (II) in which $R^3$ and $R^4$ each represent an alkyl radical containing 12 to 22 carbon atoms and $R^5$ represents a hydrogen atom, or either $R^1$ or $R^2$ represent a radical of general formula (III) in which $R^6$—X— and $R^7$—X— each represent an alkanoyl radical containing 12 to 22 carbon atoms.

Especially preferred are 5-carboxyspermylglycinedioctadecylamide (DOGS) and dipalmitoylphosphatidylethanolamine 5-carboxyspermylamide (DPPES).

The synthesis of the above lipopolyamines is described in U.S. Pat. No. 5,476,962.

Further examples of lipopolyamines for use in accordance with the invention include, 2,3-dioleyl-oxy-N [2-sperminecarboxyyl-amido]ethyl-N,N-dimethyl-1-propanaminium trifluoracetate (DOSPA), 1,3-dioleoyloxy-2-(6-carboxyspermine) propylamide (DOSPER) and RPR-120535 (Ahmed et al. (2005) Pharmaceutical Research 22(6), 972-980). Structures of preferred lipopolyamines are set out in FIG. 7.

In DOSPA the linking group is

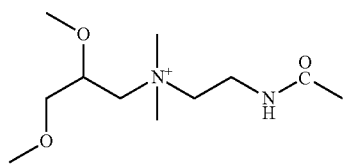

In DOSPER the linking group is

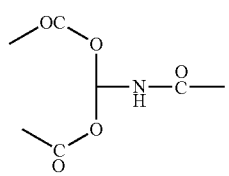

And the above structures thus represent further suitable examples of linking groups.

The lipophilic region can be as defined for $R^3$, $R^4$, $R^5$ or $R^6$ above or any saturated or unsaturated hydrocarbon chain, cholesterol or other steroid, a natural lipid or a synthetic lipid capable of forming lamellar or hexagonal phases. The length of the hydrocarbon chain may be from 10 to 30 carbons in length, e.g. 12-28, 14-26, 16-24, 18-22 carbons in length.

The carrier is preferably JetSI™ or JetSI-ENDO™, both of which are available from Polyplus transfection. Alternatively, the carrier may be Transfectam®, available from Promega.

By liposomal formulation it is meant that the cationic charged amphiphile (i.e. the lipopolyamine) is combined with a neutral helper lipid such as DOPE (dioleoyl phosphatidylethanolamine), so as to form liposomes. As such, a non-liposomal formulation of a lipopolyamine is a lipopolyamine containing formulation in which the lipopolyamine is not present in the form of a liposome. In other words, such formulations do not contain, in addition to the lipopolyamine, any neutral helper lipids. Examples of helper lipids are neutral phospholipids, cholesterol, glycerophosphoethanolamines and diacylglycerol. Preferably the lipopolyamine formulation contains solely the lipopolyamine described herein.

It is known that in general combining transfection agents with helper lipids such as DOPE will increase transfection efficiency, and hence it is surprising that an improved, and more selective degree of inhibition can be achieved by omitting these compounds from the formulation when used in methods of the invention.

The carrier is preferably not lipofectamine 2000, lipofectin, jet PEI, or a carrier having the composition of these commercially available transfection reagents. The composition of lipofectamine 2000 is a 3:1 (w/w) liposome formulation of the polycationic lipid 2,3-dioleyloxy-N-[2(sperminecarboxamido)ethyl]-N,N-dimethyl-1-propanaminium trifluoroacetate (DOSPA) (Chemical. Abstracts Registry name: N-[2-(2,5-bis[(3-aminopropyl)amino]-1-oxpentyl-amino)ethyl]-N,N-dimethyl-2,3-bis(9-octadecenyloxy)-1-propanaminium trifluoroacetate), and the neutral lipid dioleoyl phosphatidylethanolamine (DOPE).

The composition of lipofectin is a 1:1 mix of DOTMA (1,2-dioleoyloxypropyl-3-trimethyl ammonium bromide) and DOPE (dioleoylphosphatidylethanolamine).

The carrier is also preferably not siPORT or a carrier having the composition of this commercially available transfection reagent.

In an alternative embodiment, the carrier is a polyamine compound which is cationic (and preferably protonatable) at physiological pH, e.g. polyethyleneimine (PEI). PEI exists in many different structural variants, however variants having an $M_n$ value (number average molecular weight) of 600 or more, by GPC (Gel Permeation Chromatography) are of most interest. For example, the PEI may have an $M_n$ value of 500-700, 500-750, 750-1000, 100-1250, 1000-1250, 1250-1500, 1000-20000, 1100-15000, 1200-12500, 1250-10000, 1500-7500, 1750-5000, 2000-4000 or 2500-3500.

The number average molecular weight is a way of determining the molecular weight of a polymer. Polymer molecules, even ones of the same type, come in different sizes (chain lengths, for linear polymers), so the average molecular weight will depend on the method of averaging. The number average molecular weight is the common, mean, average of the molecular weights of the individual polymers. It is determined by measuring the molecular weight of n polymer molecules, summing the weights, and dividing by n.

$$\overline{M}_n = \frac{\sum_i N_i M_i}{\sum_i N_i}$$

Linear forms of PEI or non-linear, e.g. branched PEI (which can for example be of low molecular weight of the Mw values described herein), may be used.

By branched PEI it is meant PEI which contains tertiary amine groups, as well as primary and secondary amine groups. The number of tertiary amine groups, relative to the primary and/or secondary amine groups is indicative of the amount or degree of branching in the polymer. In general, branched PEI contains primary, secondary and tertiary amine groups in a ratio of 0.5-1.5:1.5-15:0.5-1.5 e.g. 1:2:1 (i.e. a ratio of 2:1 for the secondary and tertiary amine groups), but branched PEIs with a branching structure such that they contain relatively more or fewer tertiary amine groups also exist and can be used in the present invention. Examples of alternative ratios are 1:1 to 3:1 (secondary to tertiary amine groups) e.g. 1.2:1 to 2.8:1, 1.4:1 to 2.6:1, 1.6:1 to 2.4:1, 1.8:1 to 2.2:1.

The molecular weight of the PEI is preferably lower than 30 kDa or 25 kDa, e.g. lower than 15, 10, 5 or 2 kDa.

An example of suitable PEI is available from Sigma (408719 Polyethylenimine (average Mw ~800 Da by LS, average Mn ~600 by GPC, Low molecular weight, water-free). Other commercially available PEI based regents include Poly Sciences, Inc PEI (branched, Mw 10,000), US Biological Exgen 500, Polyplus transfection jetPEI™, Sigma ESCORT™ V Transfection reagent, and Mirus TransIT-TKO®.

As described above, in a preferred embodiment, one or more betacyclodextrin amine polymers can be used as the carrier molecule, i.e. the polyamine compound is a betacyclodextrin amine polymer. Suitable betacyclodextrin amine polymers and methods of synthesising such molecules are described in Hwang et al., (2001) Bioconjugate Chem, 12, 280-90.

Suitable betacyclodextrin amine polymers and a schematic showing their synthesis from appropriate monomers are set out below:

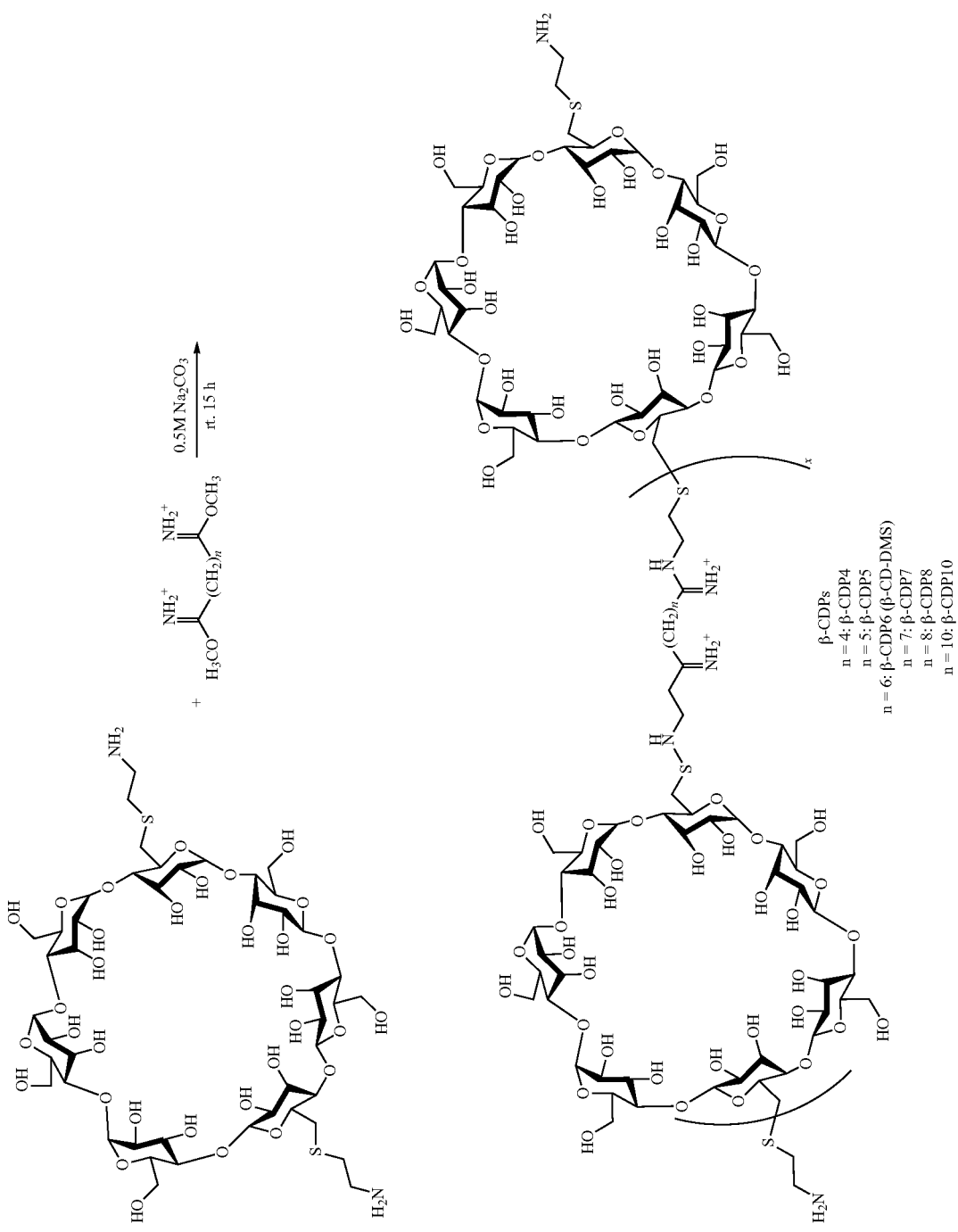

As set out above, n can be an integer from 4 to 10, inclusive, preferably 5 to 8 inclusive, or 6 to 7 inclusive. It is most preferably 4, 6 or 8. X can be any integer. X is preferably 1 to 100, 10 to 50, 15 to 25, 1 to 20, e.g. 2 to 15, 3 to 12, 4 to 10, 5 to 8 or 6 to 7 inclusive. X is most preferably 4 or 5.

In a further preferred embodiment, one or more amine group containing dendrimers (e.g. a poly amido amide (PAMAM) dendrimer) can be used as the carrier molecule, i.e. the polyamine compound is an amine group containing dendrimer. Dendrimers represent a class of macromolecular architecture called "dense star" polymers.

Unlike classical polymers, dendrimers have a high degree of molecular uniformity, narrow molecular weight distribution, specific size and shape characteristics, and a highly-functionalized terminal surface. Dendrimers are thus artificially manufactured or synthesized molecules, which are built up from branched units or monomers to make a monodisperse, tree-like or generational structure. Synthesizing monodisperse polymers demands a high level of synthetic control which is achieved through stepwise reactions, building the dendrimer up one monomer layer, or "generation," at a time. Each dendrimer consists of a multifunctional core molecule with a dendritic wedge attached to each functional site. The core molecule is referred to as "generation 0." Each successive repeat unit along all branches forms the next generation, "generation 1," "generation 2," and so on until the terminating generation.

The manufacturing process is thus a series of repetitive steps starting with a central initiator core. Each subsequent growth step represents a new "generation" of polymer with a larger molecular diameter, twice the number of reactive surface sites, and approximately doubles the molecular weight of the preceding generation. For example, the generation of the PAMAM dendrimer is described in Esfand et al., (2001) Drug Discovery Today, 6(8), 427-36 and in Kukowska-Latallo et al., (1996), *Proc. Natl. Acad. Sci. USA* 93(10), 4897-902.

Suitable dendrimers include all dendrimers containing amine groups, e.g. dendrimers with triethanolamine, $NH_3$, or ethylenediamine cores to which amine containing monomers are attached. Particularly preferred are PAMAM dendrimers. Preferably, the dendrimer is made up to polyamine monomers, e.g. having the general formula $H_2N$—$(CH_2)_m$—NH—$(CO)_n$—$(CH_2)_o$ wherein m and o are integers from 1 to 10, preferably 1 or 2 and n is 0 or 1.

Figure 14:
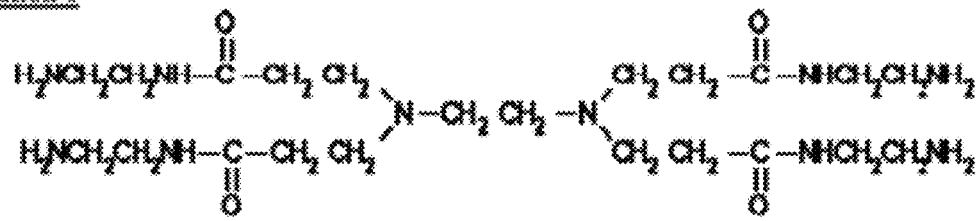
Figure 14:
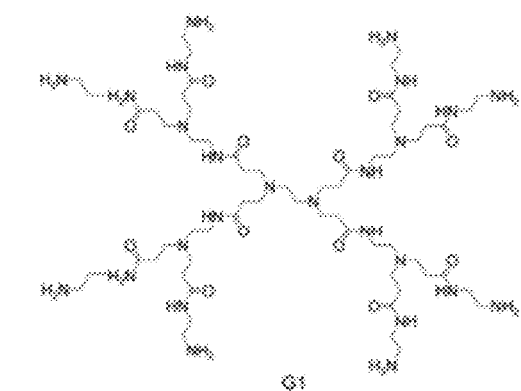
Figure 14:
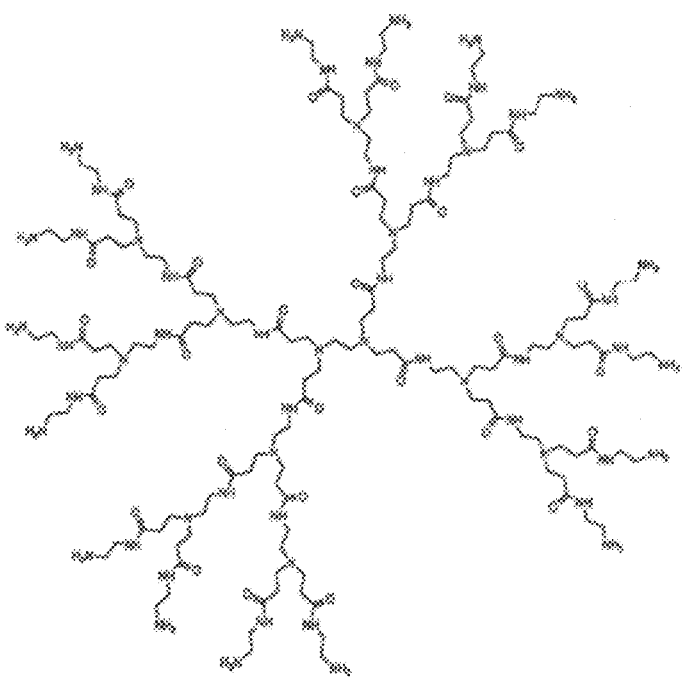

PAMAM dendrimers are shown in FIG. 14. Each "generation" represents the addition of two new $H_2N$—$CH_2$—$CH_2$—NH—CO—$CH_2$—$CH_2$— groups to each of the terminal amino groups of the preceding generation; as also illustrated in the Figure. The Table below shows the calculated properties of amine surface functional PAMAM dendrimers by generation.

| Generation | Molecular Weight | Measured Diameter (A) | Surface Groups |
|---|---|---|---|
| 0 | 517 | 15 | 4 |
| 1 | 1,430 | 22 | 8 |
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

Preferably the PAMAM dendrimer is of molecular weight 1000-235000 or 3000-117000, e.g. 6000-60000 or 14000-30000 Da.

Dendrimers can also be defined with reference to their generation, and as such the dendrimer (e.g. the PAMAM dendrimer) is preferably of generation 0, 1, 2, 3, 4, 5, 6, 7, 8, 9 or 10, particularly generation 2-6.

As mentioned above, in a further alternative embodiment, one or more cationic polypeptides can be used as the carrier molecule, i.e. the polyamine compound is a cationic polypeptide. Various cationic peptides are known in the art.

A "peptide" as defined herein includes any molecule containing any number of amino acids, i.e. one or more amino acids. Preferably however the peptide is a polymer of consecutive amino acids.

The peptides may be prepared by any convenient means, e.g. direct chemical synthesis or by recombinant means by expressing a nucleic acid molecule of the appropriate sequence in a cell.

As referred to herein in reference to peptides, "cationic" denotes that the overall, or net, charge of the peptide is +1 or higher at physiological pH, i.e. pH 7.2. An amino acid is considered +1 if the predominant species at physiological pH is positively charged when present in the context of the peptide. Each such amino acid in a peptide contributes a further positive charge to calculate the final charge of the peptide. The peptide may contain one or more negatively charged amino acid residues, as well as neutral residues, as long as the net charge of the peptide (calculated by adding together the charge attributed to each amino acid) is positive.

The charge of the peptide therefore depends on its amino acid composition. Certain amino acids are charged at normal physiological pH. Positively charged amino acids are lysine (K), arginine (R) and histidine (H) and are considered to be +1 on the above-described scale. Aspartic acid (D) and glutamic acid (E) carry a negative charge at most physiological pHs and are considered −1 on the above scale. Other naturally occurring amino acids are considered to carry no charge. Any number of positively charged or negatively charged amino acids may be present, as long as the overall charge of the peptide is +1 or more.

The amino acids used in peptides for use in the invention need not necessarily be naturally occurring amino acids. One of more of the amino acids in the peptide may be substituted for a non-naturally occurring, e.g. a derivatized amino acid. Such amino acids would similarly be assessed on the basis of their contribution to the charge of the peptide. Thus, as with naturally occurring amino acids, if the predominant species is positive at physiological pH, whether or not that charge is derived from the derivatized portion (e.g. an introduced amine group) or a portion also present in the natural amino acid is irrelevant as long as the overall charge is +1 Or more.

The charge of the peptide is >1, preferably from +1 to +1000, from +1 to +500, from +1 to 250 or from +1 to +100, e.g. +2 to +80, such as +3 to +60 or +4 to +50, +5 to +30, +6 to +20 e.g. +10 or +15.

Preferably the cationic peptide comprises L or D lysine, L or D arginine, L or D histidine and/or ornithine residues.

Even more preferably the peptide is rich in one or more of these residues e.g. comprises 10-100%, 20-80%, 30-70%, 40-60% or 50% positively charged residues. Examples of such peptides include Poly-L-Lysine, Poly-D-Lysine, Poly-Histidine, Histidylated poly-lysine and Poly-ornithine or copolymers of L or D lysine, L or D arginine, L or D histidine and/or ornithine residues with other amino acids e.g. one or more of Alanine, Asparagine, Aspartic acid, Cysteine, Glutamic acid, Glutamine, Glycine, Isoleucine, Leucine, Methionine, Phenylalanine, Proline, Serine, Threonine, Tryptophan, Tyrosine and Valine.

Said cationic polypeptides can be defined in terms of their molecular weight. As such they are preferably at least 1000 Da, 1500 Da, 2000 Da, 2500 Da, 5000 Da, 7500 Da, 10000 Da, 15000 Da, 20000 Da, 25000 Da, 30000 Da, 40000 Da, 50000 Da, 60000 Da, 70000 Da, 80000 Da, 90000 Da or 100000 Da in weight.

Alternatively the cationic polypeptides can be defined in terms of their length. Preferred cationic polypeptides are at least 10, 20, 30, 40, 50, 60, 70, 80, 90, 100, 120, 150, 200, 250, 300, 350, 400, 450, 500 amino acids in length.

A highly preferred cationic peptides is polyarginine, particularly polyarginine with a Mw of at least 15000 kDa.

Although not wishing to be bound by theory, the association of the carrier with the siRNA molecule is thought to be based on the interaction of the positively charged carrier with the negatively charged siRNA molecule, leading to the formation of an siRNA-carrier complex. The siRNA-carrier complexes interact with anionic proteoglycans at the cell surface and are taken up by endocytosis.

In general the association, binding or conjugation of the carrier with the siRNA molecule or both the siRNA and the photosensitizing agent is achieved by simply mixing the two components under appropriate conditions and concentrations and allowing the components to interact. In a preferred embodiment therefore the method comprises the additional step of contacting said siRNA with said carrier. The conditions under which this contacting step is carried out, and appropriate concentrations for each of the carrier and the siRNA molecule can readily be determined by the person skilled in the art by carrying out routine testing. Examples of suitable conditions are as set out in the Examples. For example, the siRNA molecule and the carrier molecule may be mixed together, e.g. by vortexing, and allowed to stand, e.g. at room temperature. The siRNA molecule and the carrier molecule may then be left for approximately 10-20, 10-30 or 20-40 minutes before being contacted with the cell.

Preferably 10 nM-200 nM, e.g. 15-150 nM, 20-100 nM, 20-100 nM, 30-90 nM, 40-80 nM, or 50-70 nM siRNA is used for transfection, e.g. in a well of a standard 6 well plate, although different concentrations may be tested. It is a matter of routine to determine the optimum concentration of siRNA to be used in the method.

The cells to which the siRNA and carrier are applied are prepared using standard cell culture techniques. If the cells are adherent cells they are preferably at 50-70% or 25-50% confluence.

The carrier and the siRNA molecule may be mixed in various ratios, based on standard protocols. For example, as set out in Examples 1 to 6, 8.4 µl of 2 mM carrier made up in an aqueous solution can be mixed with 2.8 µg siRNA in 2 ml medium for application to a 6 well plate. Similarly, 4.2 µl of 2 mM carrier made up in an aqueous solution can be mixed with 1.4 µg siRNA in 1 ml medium for application to a 6 well plate. The carrier need not always be at 2 mM, suitable ranges include 0.5-5 mM, 1-3 mM, 1.5-2.5 mM (e.g. made up in an aqueous solution). For every ng of siRNA, an amount equivalent to approximately 6 nanomoles of carrier (e.g. 1-10, 2-8) total in the solution with the photosensitiser can be used.

For PET, preferred concentrations are 1 µg/ml and 10 µg/ml (e.g. 0.5-20 or 1-15 µg/ml) with 100 nM siRNA, e.g. in 1 ml medium for application to a 6 well plate. This has been shown to be particularly effective for PEI with a molecular weight of 1200-25000 Daltons (e.g. 1300-2000 Daltons) as set out in Example 9. The concentration of PEI used can be modified to achieve the charge ratio and/or N/P ratio that is achieved using the conditions set out in Example 9.

For betacyclodextrin amine polymers, a suitable concentration is 100 µg/ml (e.g. 10-1000, 20-800, 30-600, 40-400, 50-200 µg/ml) with 50 nM siRNA, e.g. in 1 ml medium for application to a 6 well plate. This is based on the use of the polymer as described in Example 11. The values of n and X will influence the charge of the molecule and as such different concentrations may be appropriate. The concentration of betacyclodextrin amine polymer used can be modified to achieve the charge ratio and/or N/P ratio that is achieved using the conditions set out in Example 11.

For amine group containing dendrimers, a suitable concentration is 100 µg/ml (e.g. 10-1000, 20-800, 30-600, 40-400, 50-200 µg/ml) with 100 nM siRNA, e.g. in 1 ml medium for application to a 6 well plate. The concentration of amine group containing dendrimer used can be modified to achieve the charge ratio and/or N/P ratio that is achieved using the conditions set out in Example 12.

For cationic peptides, a suitable concentration is 0.35 µg/ml or 0.7 µg/ml (e.g. 0.1-20, 0.2-15, 0.3-10 µg/ml) with 100 nM siRNA, e.g. in 1 ml medium for application to a 6 well plate. As set out in Example 13, these concentrations were used successfully With polyarginine carrier of molecular weight 15000-70000 and >70000. The molecular weight and amino acid composition of the peptide will influence the charge of the molecule and as such different concentrations may be appropriate. The concentration of cationic peptide used can be modified to achieve a charge ratio and/or N/P ratio as is achieved using the conditions set out in Example 13.

The ratio of the two components may be expressed as the ratio of charges, and this also needs to be taken into account. Preferably the charge ratio between the carrier and the siRNA is at least 1+/− (i.e. 1 positive charge per negative charge), 5+/−, 10+/, 20+/−, 30+/−, 40+/−, 50+/−, 60+/−, 70+/−, 80+/−, 90+/−, 100+/−; 200+/−, 300+/−, 400+/− or 500+/−.

The charge ratio depends on the charge of each component (i.e. the siRNA and the carrier) and on the amount of each component that is present.

Alternatively, the ratio of the two components may be expressed as the N/P ratio, i.e. the ratio of nitrogen residues to oligonucleotide phosphate. Since not every nitrogen atom of a carrier is always a cation, the N/P ratio is not the same as the charge ratio. The N/P ratio depends on the chemical composition of each compound and on the amount of each compound that is present. Suitable values for the N/P ratio include 1-500, e.g. 2-450, 3-400, 4-350, 5-300, 6-250, 7-200, 8-150, 9-100, 10-80, 15-60, 20-50, 30-40, 1-25, 1-20, 1-15, 1-10, 1-5.

Preferably the carrier is such that at the concentration that is chosen for use, there is no release from intracellular compartments without the irradiation step of PCI, and release from intracellular compartments is seen following the irradiation step of PCI. Suitable concentrations and ratios of siRNA and carrier are mentioned above.

The carrier is in general formulated for transfection purposes in an aqueous solution (e.g. in water). Stock solution (e.g. 20 mM in Ethanol) can then be diluted (e.g. in water) to an appropriate concentration for use. U.S. Pat. No. 5,476,962 describes the formulation of lipopolyamines.

As mentioned above, the siRNA carrier may also be used as a carrier for the photosensitising agent. Alternatively, however the photosensitiser may be used without a carrier or with an alternative carrier not used according to the invention for siRNA. Such alternative carriers are referred to herein as photosensitizer carriers and include polycations such as polylysine (e.g. poly-L-lysine or poly-D-lysine), polyethyleneimine or dendrimers (e.g. cationic dendrimers such as SuperFect7); cationic lipids such as DOTAP or Lipofectin and peptides.

In order to target the siRNA molecule and/or the photosensitizing agent to specific cells (e.g. cancer cells) or tissues, the siRNA molecule and/or the photosensitizer and/or the carrier may be associated or conjugated to specific targeting molecules that will promote the specific cellular uptake of the siRNA molecule into desired cells or tissues.

Many different targeting molecules can be employed, e.g. as described in Curiel (1999), Ann. New York Acad. Sci. 886, 158-171; Bilbao et al., (1998), in Gene Therapy of Cancer (Walden et al., eds., Plenum Press, New York); Peng and Russell (1999), Curr. Opin. Biotechnol. 10, 454-457; Wickham (2000), Gene Ther. 7, 110-114.

The targeting molecule may be associated, bound or conjugated to the siRNA molecule, to the carrier, to the photosensitising agent or to two (e.g. the siRNA and the carrier or the siRNA and the photosensitising agent or the carrier and the photosensing agent) or all three of these moieties, and the same or different targeting molecules may be used. As mentioned above, more than one targeting molecule may be used simultaneously.

The method of the invention may be put into practice as described below. In the method of the invention, the siRNA molecule, together with its carrier and a photosensitising compound (optionally with the same carrier or with a photosensitizer carrier) are applied simultaneously or in sequence to the cells, whereupon the photosensitizing compound, carrier and the siRNA molecule are endocytosed or in other ways translocated into endosomes, lysosomes or other intracellular membrane restricted compartments.

The siRNA, carrier and the photosensitising compound may be applied to the cells together or sequentially. In general the siRNA is mixed with the carrier as described above so as to form a complex, which is then administered to the cell simultaneously with the photosensitising compound. Alternatively, the siRNA:carrier complex and the photosensitising compound can be administered sequentially. The siRNA-carrier complex and the photosensitising compound may be taken up by the cell into the same or different intracellular compartments (e.g. they may be co-translocated).

The siRNA is then released by exposure of the cells to light of suitable wavelengths to activate the photosensitising compound which in turn leads to the disruption of the intracellular compartment membranes and the subsequent release of the siRNA, which may be located in the same compartment as the photosensitizing agent, into the cytosol. Thus, in these methods the final step of exposing the cells to light results in the siRNA being released from the same intracellular compartment as the photosensitizing agent and becoming present in the cytosol.

WO 02/44396 (which is incorporated herein by reference) describes a method in which the order of the steps could be changed such that for example the photosensitising agent is contacted with the cells and activated by irradiation before the molecule to be internalised (and the carrier) are brought into contact with the cells. This adapted method takes advantage of the fact that it is not necessary for the molecule to be internalised to be present in the same cellular subcompartment as the photosensitising agent at the time of irradiation.

Thus in a preferred embodiment, said photosensitising agent, said carrier and said siRNA molecule (e.g. as a carrier:siRNA complex) are applied to the cell together, or said photosensitising agent is applied separately relative to said carrier and said siRNA molecule. As a consequence they may be taken up by the cell into the same intracellular compartment and said irradiation may then be performed. The photosensitising agent, carrier and siRNA molecule can be separate, or they can be formulated as a dendrimeric molecule (see e.g. Nishiyama N et al., (2005) Nat. Mater. 4(12):934-41)

In an alternative embodiment, said method can be performed by contacting said cell with a photosensitising agent, contacting said cell with the carrier and the siRNA molecule to be introduced and irradiating said cell with light of a wavelength effective to activate the photosensitising agent, wherein said irradiation is performed prior to the cellular uptake of said siRNA molecule and said carrier into an intracellular compartment containing said photosensitising agent, preferably prior to cellular uptake of said molecule and said carrier into any intracellular compartment.

Said irradiation can be performed after the cellular uptake of the molecule and the carrier molecule into an intracellular compartment, whether or not said siRNA molecule and the photosensitising agent are localised in the same intracellular compartments at the time of light exposure. In one preferred embodiment however irradiation is performed prior to cellular uptake of molecule to be internalised.

"Internalisation" as used herein, refers to the cytosolic delivery of molecules. In the present case "internalisation" thus includes the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cells with a photosensitising agent and with the siRNA molecule and carrier may be carried out in any convenient or desired way. Thus, if the contacting step is to be carried out in vitro the cells may conveniently be maintained in an aqueous medium such as for example appropriate cell culture medium and at the appropriate time point the photosensitising agent and/or siRNA molecule and carrier can, simply be added to the medium under appropriate conditions, for example at, an appropriate concentration and for an appropriate length of time. For example, the cells may be contacted with the siRNA molecule and carrier in the presence of serum-free medium.

The photosensitizing agent is brought into contact with the cells at an appropriate concentration and for an appropriate length of time which can easily be determined by a skilled person using routine techniques and will depend on such factors as the particular photosensitizing agent used and the target cell type and location. The concentration of the photosensitizing agent must be such that once taken up into the cell, e.g. into, or associated with, one or more of its intracellular compartments and activated by irradiation, one or more cell structures are disrupted e.g. one or more intracellular compartments are lysed or disrupted. For example photosensitising agents as described herein may be used at a concentration of for example 10 to 50 µg/ml. For in vitro use the range can be much broader, e.g. 0.05-500 µg/ml. For in vivo human treatments the photosensitizing agent may be used in the range 0.05-20 mg/kg body weight when administered systemically or 0.1-20% in a solvent for topical application. In smaller animals the concentration range may be different and can be adjusted accordingly.

The time of incubation of the cells with the photosensitizing agent (i.e. the "contact" time) can vary from a few minutes to several hours, e.g. even up to 48 hours or longer, e.g. 12 to 20 or 24 hours. The time of incubation should be such that the photosensitizing agent is taken up by the appropriate cells, e.g. into intracellular compartments in said cells.

The incubation of the cells with the photosensitizing agent may optionally be followed by a period of incubation with photosensitiser-free medium before the cells are exposed to light or the siRNA molecule and carrier are added, e.g. for 10 minutes to 8 hours, especially 1 to 4 hours.

The siRNA molecule and carrier (e.g. as a preformed siRNA:carrier complex) are brought into contact with the cells at an appropriate concentration and for an appropriate length of time.

Determining the appropriate doses of siRNA molecules for use in the methods of the present invention is routine practice for a person skilled in the art. For in vitro applications an exemplary dose of the siRNA molecules would be approximately 1-100 nM siRNA and for in vivo applications approximately $10^{-6}$-1 g siRNA per injection in humans. For example, siRNA molecules may be administered at levels of less than 500 nM, e.g. less than 300 nM, especially preferably less than 100 nM or 50 nM, for example from 1 to 100 nM, or 5 to 50 nM, where the concentration indicated reflects the levels in contact with the cell.

As mentioned above, it has been found that the contact may be initiated even several hours after the photosensitising agent has been added and irradiation taken place.

An appropriate concentration can be determined depending on the efficiency of uptake of the siRNA molecule in question into the cells in question and the final concentration it is desired to achieve in the cells. Thus "transfection time" or "cellular uptake time" i.e. the time for which the molecules are in contact with the cells can be a few minutes or up to a few hours, for example a transfection time of from 10 minutes until up to 24 hours, for example 30 minutes up to 10 hours or for example 30 minutes until up to 2 hours or 6 hours can be used. Longer incubation times may also be used, e.g. 24 to 96 hours or longer, e.g. 5-10 days.

An increased transfection time usually results in increased uptake of the molecule in question. However, shorter incubation times, for example 30 minutes to 1 hour, can also result in an improved specificity of the uptake of the molecule. Thus, in selecting a transfection time for any method, an appropriate balance must be struck between obtaining a sufficient uptake of the molecule while maintaining sufficient specificity of the PCI treatment.

In vivo an appropriate method and time of incubation by which the siRNA molecule, carrier and photosensitizing agents are brought into contact with the target cells will be dependent on factors such as the mode of administration and the type of siRNA molecule, carrier and photosensitizing agents. For example, if the siRNA molecule and carrier are injected into a tumour, tissue or organ which is to be treated, the cells near the injection point will come into contact with and hence tend to take up the siRNA molecule more rapidly than the cells located at a greater distance from the injection point, which are likely to come into contact with the siRNA molecule at a later time point and lower concentration.

In addition, an siRNA molecule administered by intravenous injection may take some time to arrive at the target cells and it may thus take longer post-administration e.g. several days, in order for a sufficient or optimal amount of the siRNA molecule to accumulate in a target cell or tissue. The same considerations of course apply to the time of administration required for the uptake of the photosensitizing agent into cells. The time of administration required for individual, cells in vivo is thus likely to vary depending on these and other parameters.

Nevertheless, although the situation in vivo is more complicated than in vitro, the underlying concept of the present invention is still the same, i.e. the time at which the molecules come into contact with the target cells must be such that before irradiation occurs an appropriate amount of the photosensitizing agent has been taken up by the target cells and either: (i) before or during irradiation the siRNA molecule has either been taken up, or will be taken up after sufficient contact with the target cells, into the same or different intracellular compartments or (ii) after irradiation the siRNA molecule is in contact with the cells for a period of time sufficient to allow its uptake into the cells. Provided the siRNA molecule is taken up into intracellular compartments affected by activation of the photosensitizing agent (e.g. compartments in which the agent is present), the siRNA molecule can be taken up before or after irradiation.

The light irradiation step to activate the photosensitising agent may take place according to techniques and procedures well known in the art. For example, the wavelength and intensity of the light may be selected according to the photosensitising agent used. Suitable light sources are well known in the art.

The time for which the cells are exposed to light in the methods of the present invention may vary. The efficiency of the internalisation of the siRNA molecule into the cytosol increases with increased exposure to light to a maximum beyond which cell damage and hence cell death increases.

A preferred length of time for the irradiation step depends on factors such as the target, the photosensitizer, the amount of the photosensitizer accumulated in the target cells or tissue and the overlap between the absorption spectrum of the photosensitizer and the emission spectrum of the light source. Generally, the length of time for the irradiation step is in the order of minutes to several hours, e.g. preferably up to 60 minutes e.g. from 0.5 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Shorter irradiation times may also be used, for example 1 to 60 seconds, e.g. 10-50, 20-40 or 25-35 seconds.

Appropriate light doses can be selected by a person skilled in the art and again will depend on the photosensitizer and the amount of photosensitizer accumulated in the target cells or tissues. For example, the light dose typically used for photodynamic treatment of cancers with the photosensitizer Photofrin and the protoporphyrin precursor 5-aminolevulinic acid is in the range 50-150 J/cm2 at a fluence range of less than 200 mW/cm$^2$ in order to avoid hyperthermia. The light doses are usually lower when photosensitizers with higher extinction coefficients in the red area of the visible spectrum are used. However, for treatment of non-cancerous tissues with less photosensitizer accumulated the total amount of light needed may be substantially higher than for treatment of cancers. Furthermore, if cell viability is to be maintained, the generation of excessive levels of toxic species is to be avoided and the relevant parameters may be adjusted accordingly.

The methods of the invention may inevitably give rise to some cell killing by virtue of the photochemical treatment i.e. through the generation of toxic species on activation of the photosensitizing agent. Depending on the proposed use, this cell death may not be of consequence and may indeed be advantageous for some applications (e.g. cancer treatment). Preferably, however, cell death is avoided and as noted elsewhere herein the method can be carried out so as to cause strong inhibition of expression (i.e. a strong siRNA effect) in the absence of cell toxicity. It is highly advantageous to achieve a strong inhibition of expression in the absence of general cell toxicity or an effect on cell viability. The methods of the invention may be modified such that the fraction or proportion of the surviving cells is regulated by selecting the light dose in relation to the concentration of the photosensitizing agent. Again, such techniques are known in the art.

In applications in which viable cells are desirable, substantially all of the cells, or a significant majority (e.g. at least 50%, more preferably at least 60, 70, 80 or 90% of the cells) are not killed. Cell viability following PCI treatment can be measured by standard techniques known in the art such as the MTS test (see the Examples).

Regardless of the amount of cell death induced by the activation of the photosensitiser, for the siRNA to have an effect in the cells, it is important that the light dose is regulated such that some of the individual cells wherein the PCI effect is manifested are not killed by the photochemical treatment alone (although they may subsequently be killed by molecules introduced into the cells if those molecules have a cytotoxic effect).

Cytotoxic effects may be achieved by using for example gene therapy in which an siRNA molecule is internalized into a tumour cell by the method of the invention e.g. to down-regulate a gene.

The methods of the invention may be used in vitro or in vivo, for example either for in situ treatment or for ex vivo treatment followed by the administration of the treated cells to the body, for various purposes including inhibition of expression of specific gene products e.g. in gene therapy methods and the generation of screening assays.

Thus the present invention provides a method of inhibiting the expression of a target gene by introducing an siRNA molecule into a cell containing said target gene by a method as described hereinbefore, wherein said siRNA molecule specifically inhibits expression of said target gene.

"Specific inhibition" refers to sequence-dependent inhibition of the target gene. Expression of genes which contain a sequence that is sufficiently identical at the nucleic acid level to the siRNA molecule used will be affected by the siRNA molecule. As noted above, standard techniques have been developed that allow the skilled person to design siRNA molecules of appropriate sequence to cause sequence-specific inhibition of expression.

"Target gene" refers to a gene whose expression is to be down-regulated and which is to be the target of investigation or manipulation.

These methods may be used to alter the expression profile of cells, e.g. to investigate cellular pathways, or to determine the influence of expression of a particular gene, or for therapeutic purposes.

The methods of the invention may also be used in treating any disease which benefits from the down-regulation, repair or mutation of one or more genes. For example, genes that are overexpressed in cancer may be down-regulated by administering the appropriate siRNA molecule (Lage (2005) Future Oncol 1(1):103-13). Alternative diseases that may be treated include neurodegenerative diseases such as Huntington's disease and Alzheimer's disease and viral infections such as hepatitis (e.g. B and C) and HIV.

Thus, a further aspect of the invention provides a composition containing an siRNA molecule, a carrier molecule (preferably as a complex with said siRNA molecule) and optionally separately also a photosensitizing agent as described herein. In a further aspect the invention provides said composition for use in therapy.

Alternatively, the present invention provides a kit comprising an siRNA molecule, a carrier molecule and optionally also a photosensitizing agent as described herein. Preferably said kit (or product) is for simultaneous, separate or sequential use in a medical treatment.

Alternatively described, the present invention provides the use of an siRNA molecule and carrier as described herein in the preparation of a medicament for treating or preventing a disease, disorder or infection by altering expression of one or more target genes in said patient. Optionally said medicament may contain only one of said siRNA molecule or carrier and may be used in methods in which said siRNA molecule or carrier not present in said medicament is for administration to said patient when treating or preventing said disease, disorder or infection. Optionally said medicament may contain the photosensitising agent. Preferably said medicament is for gene therapy, i.e. for treating a disease or disorder which is typified by abnormal gene expression or which would benefit from suppression of one or more genes. Said alteration includes down regulation of said expression.

According to the different embodiments set out above, the said photosensitizing agent and said siRNA molecule and carrier is contacted with cells or tissues of a patient simultaneously or sequentially and said cells are irradiated with light of a wavelength effective to activate the photosensitizing agent and irradiation is performed prior to, during or after the cellular uptake of said siRNA molecule and the carrier into an intracellular compartment containing said photosensitizing agent, preferably prior to cellular uptake of said transfer molecule into any intracellular compartment.

Thus in an alternative aspect the invention provides a method of treating or preventing a disease, disorder or infection in a patient comprising introducing an siRNA molecule and carrier into one or more cells in vitro, in vivo or ex vivo according to the methods as described hereinbefore and where necessary (i.e. when transfection is conducted in vitro or ex vivo) administering said cells to said patient.

As defined herein "treatment" refers to reducing, alleviating or eliminating one or more symptoms of the disease, disorder or infection which is being treated, relative to the symptoms prior to treatment. "Prevention" refers to delaying or preventing the onset of the symptoms of the disease, disorder or infection.

Compositions of the present invention may also comprise a cell containing an siRNA molecule which has been internalised into the cytosol of said cell by a method of the invention. The invention further extends to such compositions for use in therapy, particularly cancer or gene therapy.

Thus, a yet further aspect of the invention provides a cell or a population of cells containing an siRNA molecule which has been internalised into the cytosol of said cell, which cell is obtainable by a method of the present invention.

A yet further aspect of the invention provides the use of a such a cell or population of cells for the preparation of a composition or a medicament for use in therapy as described hereinbefore, preferably cancer or gene therapy.

The invention further provides a method of treatment of a patient comprising administering to said patient cells or compositions of the present invention, i.e. a method comprising the steps of introducing an siRNA molecule into a cell as described hereinbefore and administering said cell thus prepared to said patient. Preferably said methods are used to treat cancer or in gene therapy.

In vivo, any mode of administration common or standard in the art may be used, e.g. injection, infusion, topical administration, both to internal and external body surfaces etc. For in vivo use, the invention can be used in relation to any tissue which contains cells to which the photosensitising agent and the siRNA molecule are localized, including body fluid locations, as well as solid tissues. All tissues can be treated as long as the photosensitiser is taken up by the target cells, and the light can be properly delivered.

Thus, the compositions of the invention may be formulated in any convenient manner according to techniques and procedures known in the pharmaceutical art, e.g. using one or more pharmaceutically acceptable carrier or excipients. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule, purpose of treatment, age of patient, mode of administration etc. In connection with the photosensitizing agent the potency/ability to disrupt membranes on irradiation, should also be taken into account.

The methods described above may alternatively be used to generate a screening tool for high throughput screening methods, particularly to analyze the effects of silencing a particular gene. siRNA directed to one or more specific genes may be generated and used in the method of the invention as described above. The siRNA may thus be used to reduce the expression of a gene in a population of cells. The resulting cell population may then be used as a screening tool to identify downstream effects of gene silencing, with standard techniques.

Previous attempts to reduce gene expression with normal and chemically modified antisense oligonucleotides have been limited by problems with nuclease degradation of the antisense oligonucleotides, the occurrence of non-specific effects and/or insufficient target affinity. By using the method of the invention to administer siRNA, these problems may be overcome.

Thus in a further aspect, the invention provides a method of modifying the gene expression pattern of a cell (e.g. a cell population) to prepare a cell (or cell population) for use as a screening tool (e.g. for high throughput screening), comprising contacting an siRNA molecule capable of inhibiting or reducing the expression of a gene, a carrier and a photosensitising agent with a cell (e.g. a cell population) and irradiating the cell (e.g. a cell population) with light of a wavelength effective to activate the photosensitising agent. The invention further extends to such cells and a method of screening such cells wherein specific properties of such cells, e.g. mRNA expression levels of such cells are examined, e.g. in microarrays. By "modified gene expression pattern" it is meant that as a consequence of the presence of said siRNA molecule in the cell nucleus, the transcription or translation of the gene to which it is directed is affected.

As a consequence of this change in expression of the gene, the expression of other genes may be influenced. Thus, by affecting the normal expression of the gene being studied, it is possible to determine the changes in expression pattern of other genes. The identification of these genes, and of the influence that the expression of the gene being studied has on them allows the investigator to draw conclusions about the functions of the gene e.g. their downstream functions. The genes that are affected by the change in normal expression of the gene being studied may be upregulated or downregulated, but the overall change in the pattern of expression gives an indication of the role of the gene in normal cell function and of the consequences of its misregulation.

Using standard techniques well known in the art it is possible to study the effect of the downregulation or elimination of expression of the gene in question. This may for example be done by looking for functional changes in the cells (or cell population), such as changes in cell adhesion, protein secretion or morphological changes. Alternatively, the gene expression profile can be studied directly by analysing mRNA patterns and/or protein expression, again using standard techniques that are well known in the art.

By inhibiting or reducing the expression of a gene, it is to be understood that the expression of the gene in question is reduced, when compared to a cell which has not been subjected to the method i.e. a wild-type or normal cell. The change in the level of gene expression may be determined by standard techniques known in the art.

There may be a complete inhibition of expression, such that there is no detectable expression of the gene, i.e. no mRNA or protein is detectable, or there may be a partial inhibition of expression, i.e. a reduction, whereby the amount of gene expression is lower than the wild-type or normal cell. This can be assessed and controlled for by comparing the effect of an siRNA with a specific sequence with the effect of an siRNA with a scrambled sequence i.e. the same composition of nucleotides, but in a different sequence order. Preferably for this technique to be useful, the reduction in expression is to less than or 80% of control levels, e.g. <50%, preferably <20, 10 or 5% of control levels. The cell(s) used will preferably be a cell population, the individual cells of which are genetically identical. The cells may be any cells, as discussed above.

The cell or cell population generated according to methods of the invention may be used to make a library which forms a further aspect of the invention.

The invention will now be described in more detail in the following non-limiting Examples with reference to the following drawings in which:

FIG. 1 shows the results of a gene silencing experiment using the OHS cell line with various transfection reagents with (black bars) and without (white bars) PCI treatment using siRNA9. Graph displays S100A4 protein levels, from left to right; 1) siPORT Lipid, 2) FuGene 6, 3) Lipofectamine 2000, 4) Lipofectin, 5) jetSI and 6) jetSI-ENDO. Results are represented as percent of untreated control cells.

The bars are the mean from three individual experiments. Error bars show standard error of the mean (SEM).

Figure 2A:
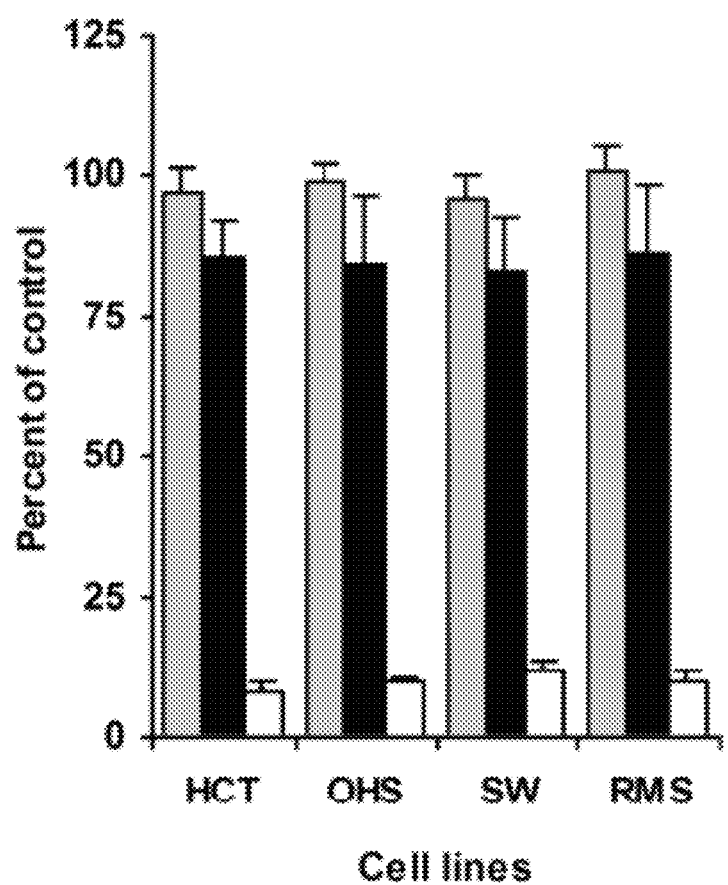
Figure 2B:
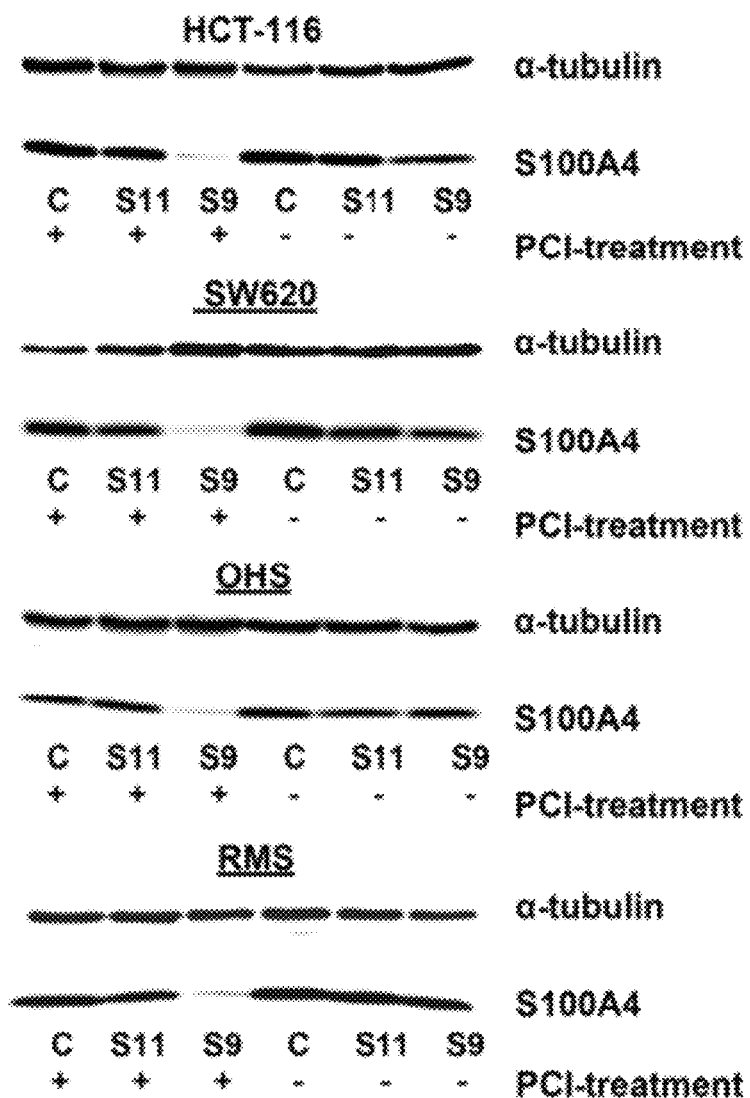

FIGS. 2A-2B show the results of a gene silencing experiment where cells of different types were transfected with siRNA using jetSI®-ENDO, with and without PCI treatment. The results in (A) display S100A4 protein levels in four cell lines when treated with siRNA. Grey bars show scrambled control siRNA with PCI, black bars display effector siRNA without PCI and white bars display effector siRNA with PCI. Cell lines from left to right, HCT-116, SW620, OHS and RMS. The bars are the mean from three individual experiments. Error bars show standard error of the mean (SEM). The results in (B) show a Western blot showing different cell lines from the top to the bottom, HCT-116, SW620, OHS and RMS. The upper panel displays α-tubulin loading control and the lower panel S100A4 levels. In each lower panel, lanes 1-3 show protein levels without PCI treatment: untreated control (C), scrambled control (siRNA11), and effector (siRNA9). Lanes 4-6, show protein levels with PCI treatment: untreated control (C), scrambled control (siRNA11), and effector (siRNA9).

Figure 3A:
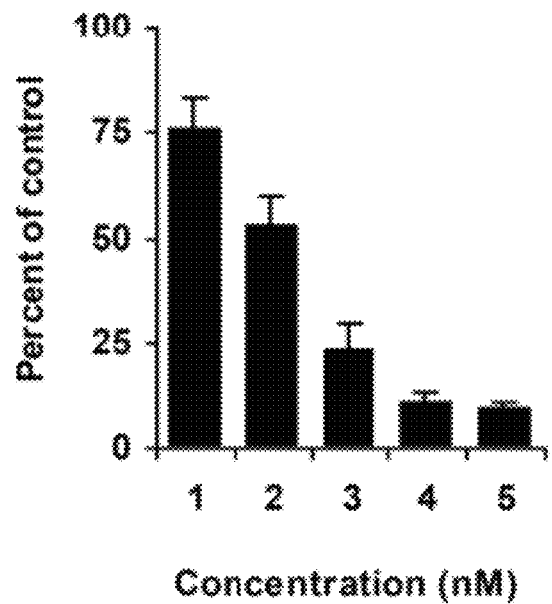
Figure 3B:
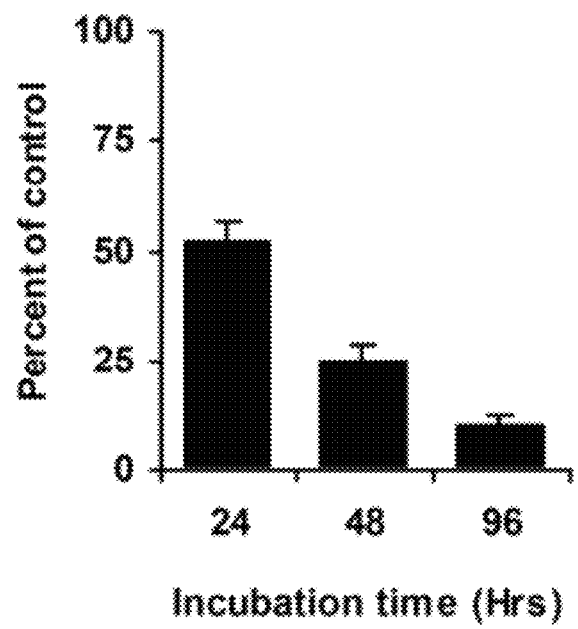

FIGS. 3A-3B show results of a gene silencing experiment in OHS cells A) Dose-dependent silencing (1-5 nM siRNA) 96 hrs after irradiation: B) Time-dependent silencing (24, 48 and 96 hrs) with siRNA9. Results are represented as percent of untreated control cells. The bars are the mean from three individual experiments. Error bars show standard error of the mean (SEM).

Figure 4A:
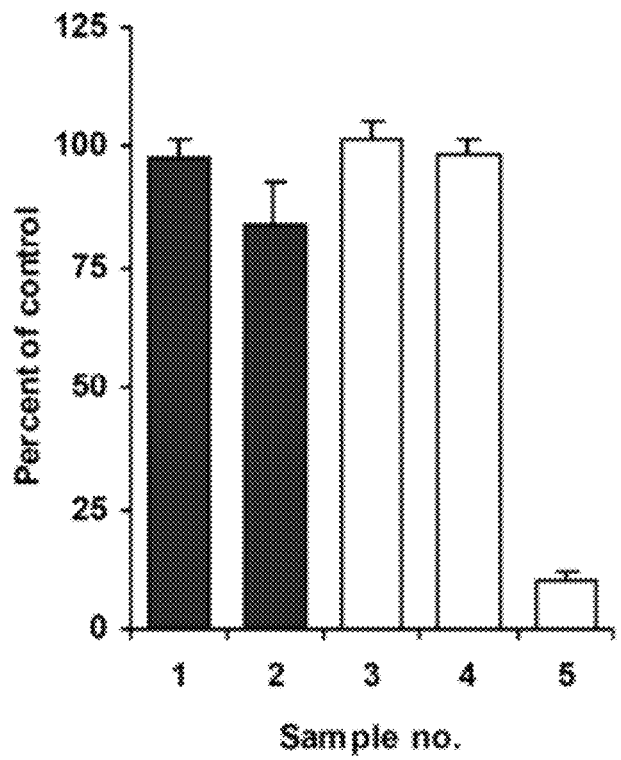
Figure 4B:
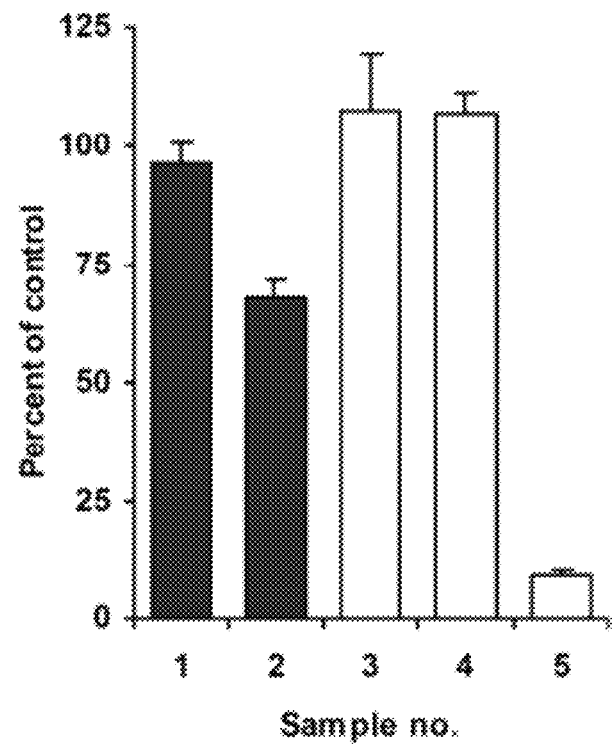

FIGS. 4A-4B show the results of gene silencing with siRNA transfected with jetSI®, with and without PCI treatment 96 hrs after irradiation. Results show S100A4 protein level (A) and RNA levels (B) after treating the OHS cell line with 100 nM siRNA as indicated below. Black bars represent samples without PCI, and white bars represent samples subjected to PCI. Untreated control without PCI treatment was used as control for all samples (not shown). Samples: 1 and 4) scrambled control (siRNA11), 2 and 5) effector (siRNA9), 3) untreated control. The bars represent the mean from three individual experiments. Error bars show standard error of the mean (SEM).

Figure 5:
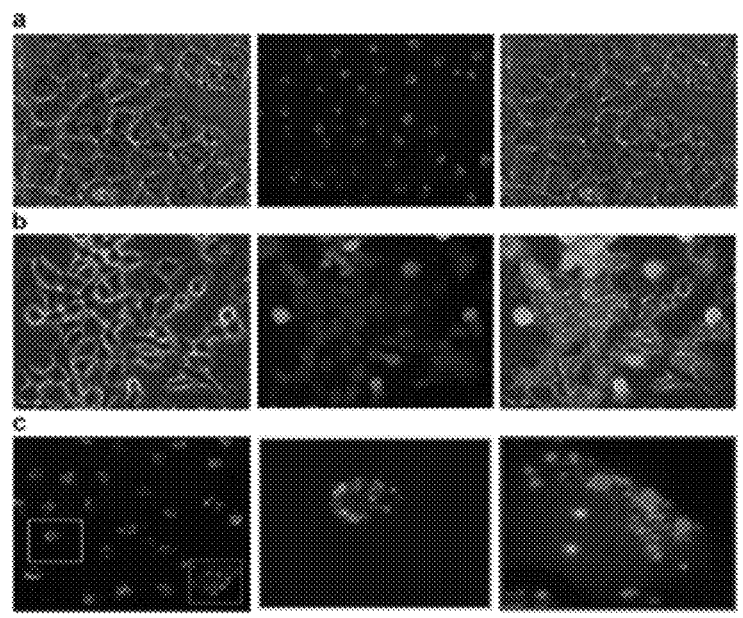

FIG. 5 shows the distribution of fluorescence labelled siRNA in OHS following transfection (200 nM) with jetSI-ENDO, with and without PCI treatment a) Delivery of siRNA without PCI treatment, from left to right: phase contrast, fluorescence and the corresponding merge. b) Delivery of siRNA with PCI treatment: from left to right: phase contrast, fluorescence and the corresponding merge. c) Fluorescence pictures without PCI treatment displaying from left to right: fluorescence entrapped in endosomes (left hand box) and fluorescence leakage from endosomes (right hand box), enlargement of the image within the left hand box, and enlargement of the image within the right hand box.

Figure 6:
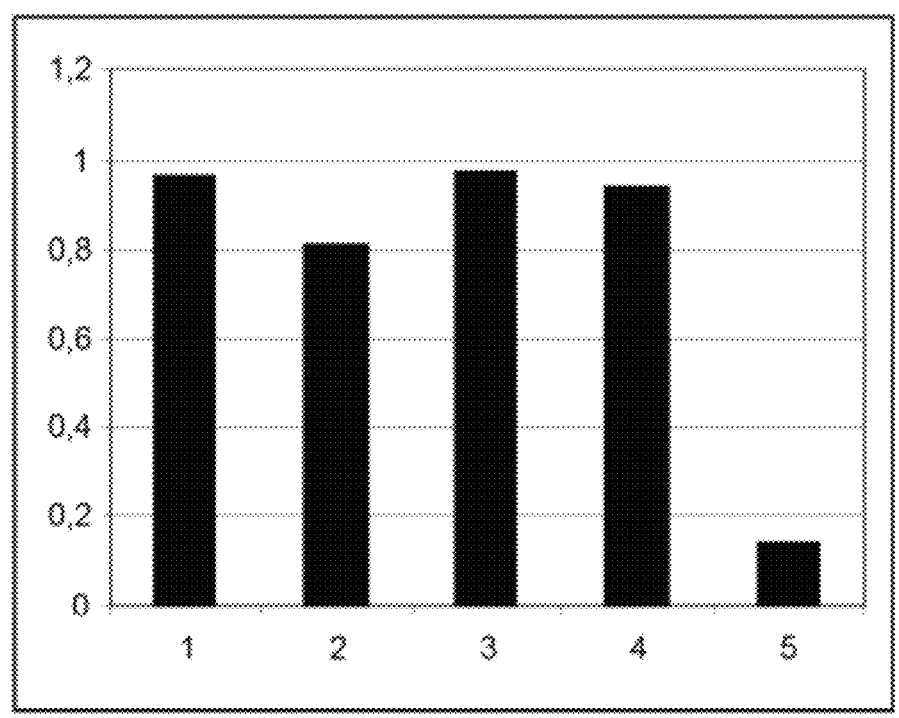
Figure 7A:
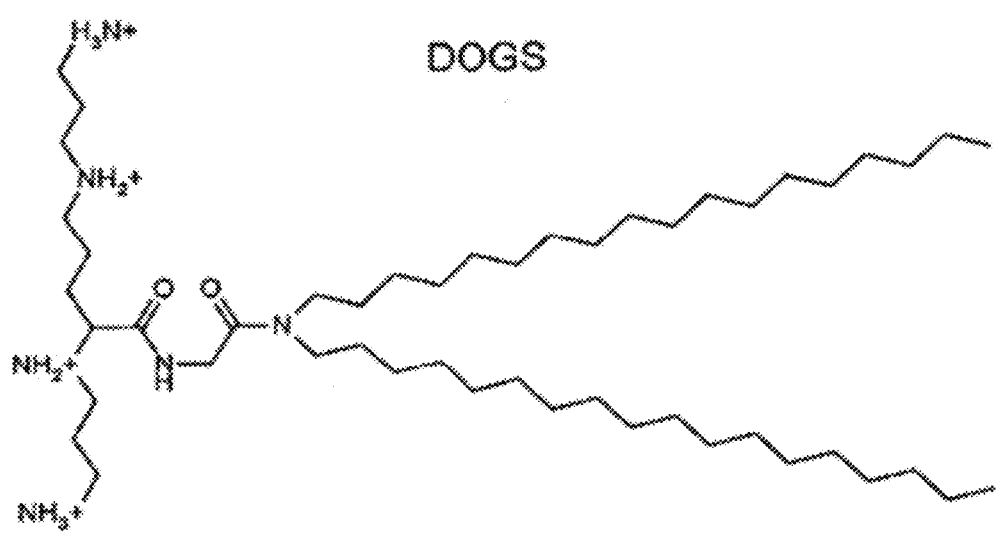
Figure 7B:
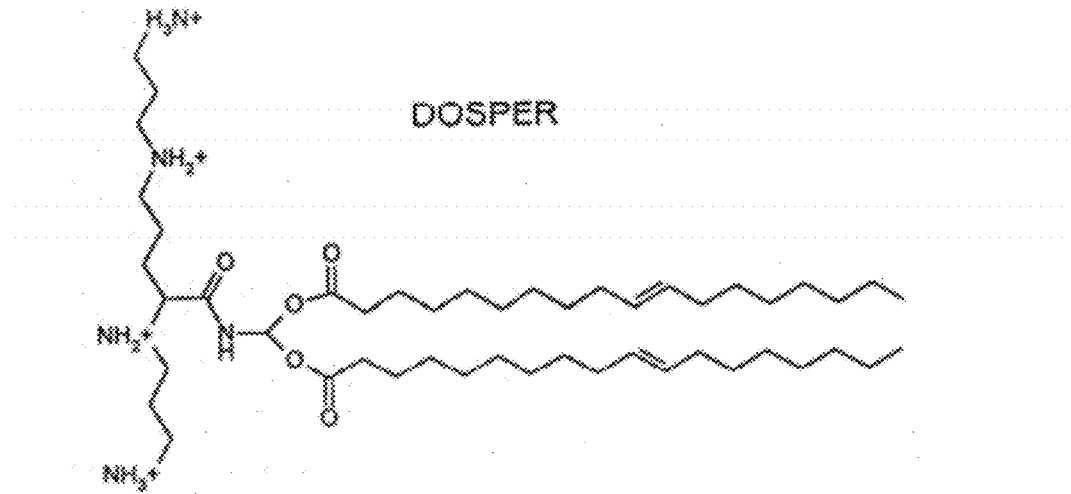
Figure 7C:
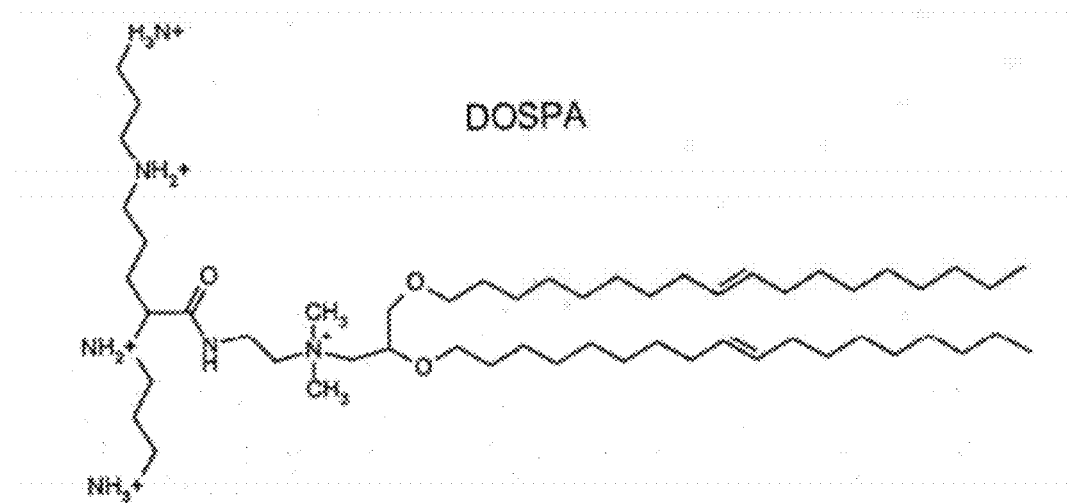
Figure 7D:
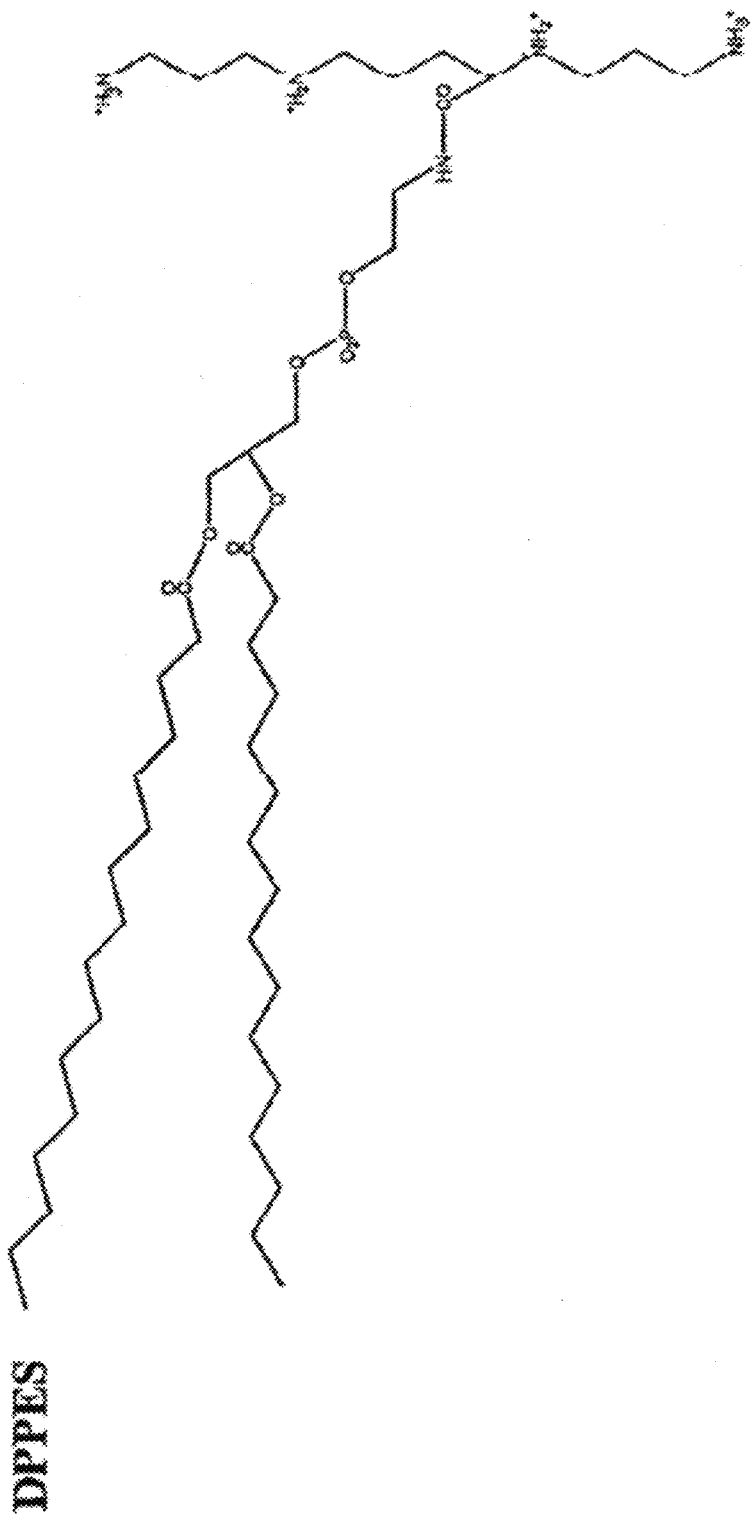
Figure 7E:
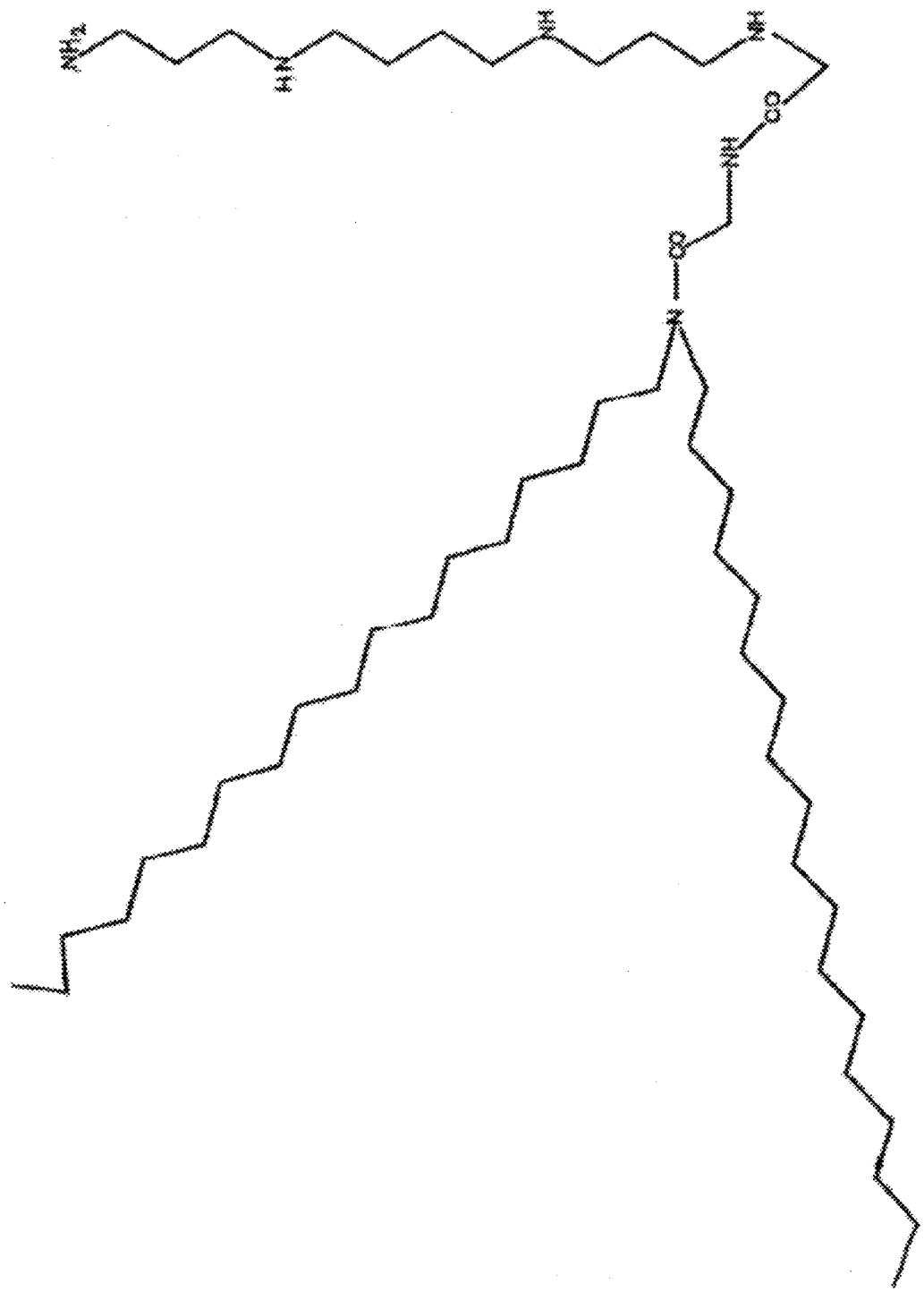

FIG. 6 shows the results of gene silencing using jetSI after treating OHS with 100 nM siRNA and jetSI at 50% of the level recommended compared to the standard protocol. Bars represent; 1) scrambled control siRNA without PCI, 2) effector siRNA without PCI, 3) untreated control with PCI, 4) scrambled control siRNA with PCI, 5) effector control siRNA with PCI. The bars represent the mean from three individual experiments.

FIGS. 7A-7E show the structures of preferred lipopolyamines. (See also Ahmed et al, supra and Behr et al (1989) PNAS, 86, 6982-6).

Figure 8:
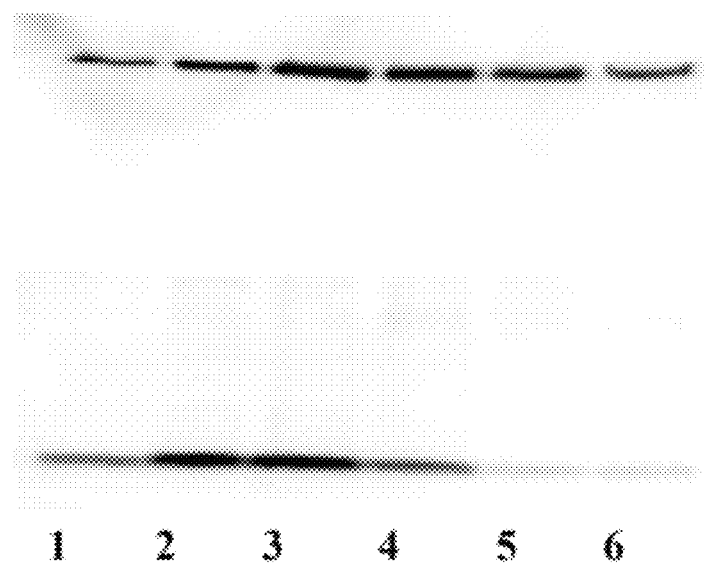

FIG. 8 shows the results of gene silencing using PEI as the carrier. The Western blot displays a loading control (alpha-tubulin) in the upper panel and S100A4 protein levels in the lower panel. Lane 1=untreated control (without PEI), 2=1 µl PEI+effector siRNA, 3=10 µl PEI+effector siRNA, 4=untreated control (without PEI), 5=1 µl PEI+effector siRNA, 6=10 µl PEI+effector siRNA. Lanes 1-3 are without PCI, and lanes 4-6 are with PCI.

Figure 9:
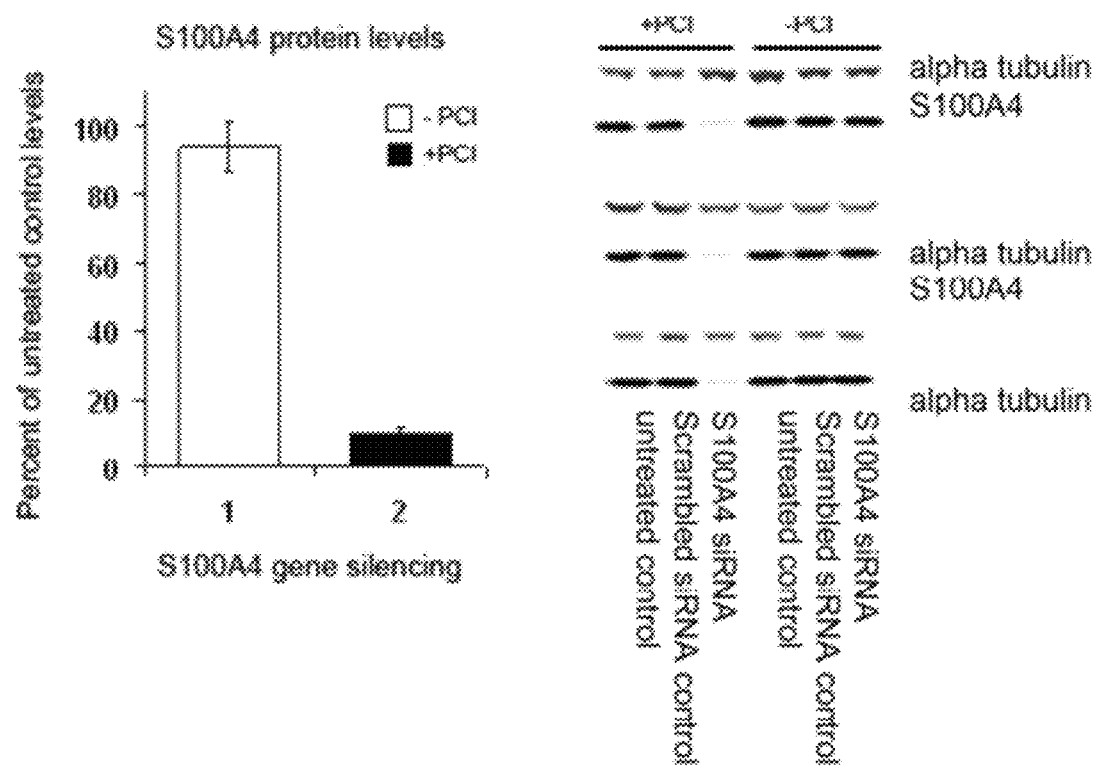

FIG. 9 shows the results of gene silencing using 25 kDa PEI as the carrier. The samples used are indicated on the Figure. A. S100A4 protein level quantified by scanning of Western blots (using S100A4 siRNA with or without PCI-mean of 3 individual experiments where error bars represent SEM). B. An example of a Western blot.

Figure 10:
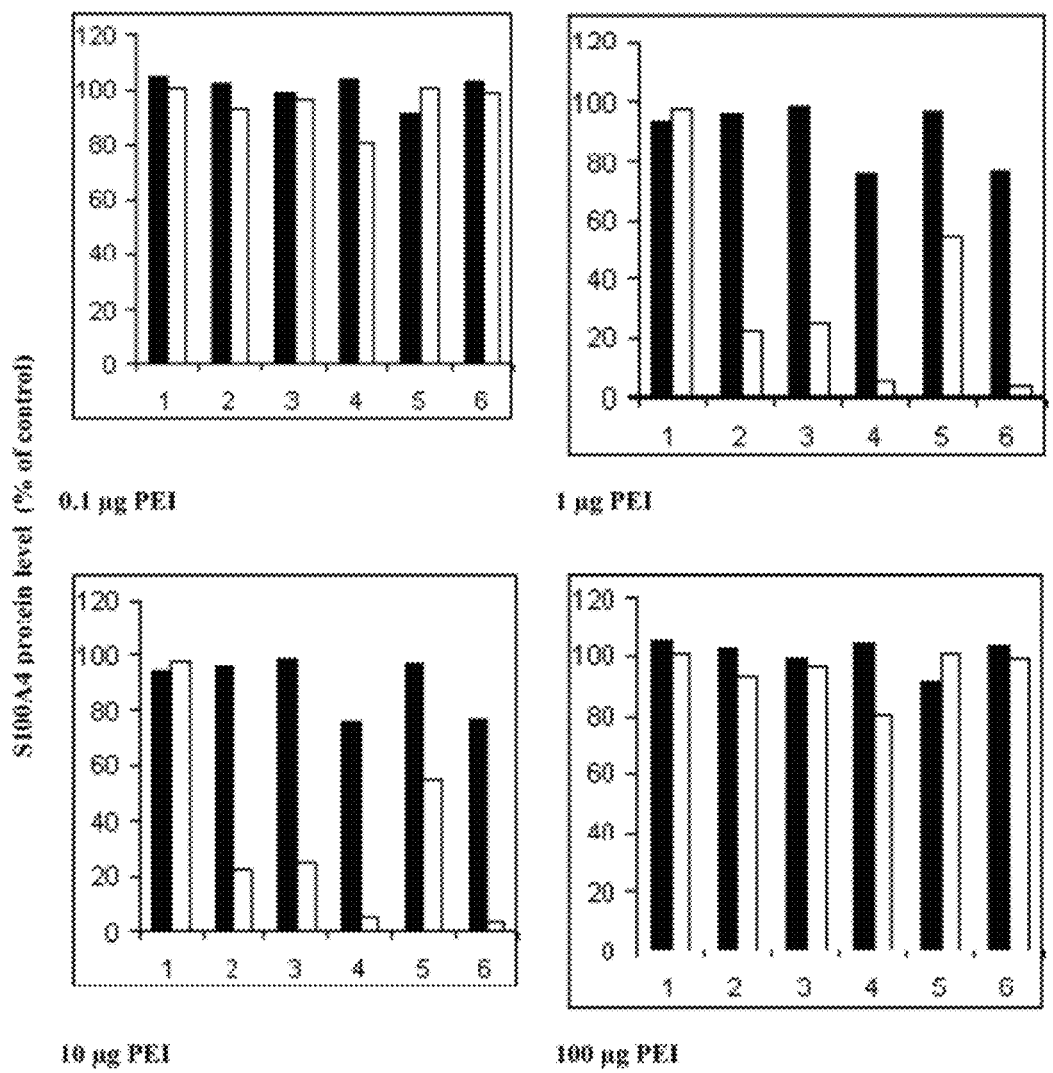

FIG. 10 shows the effect of PCI on siRNA activity with different PEI carriers used in different concentrations. S100A4 protein levels were quantified by scanning of Western blots. Black bars represent transfections without PCI, while white bars represent transfection with PCI. The results are the mean of 3 individual experiments.

Figure 11:
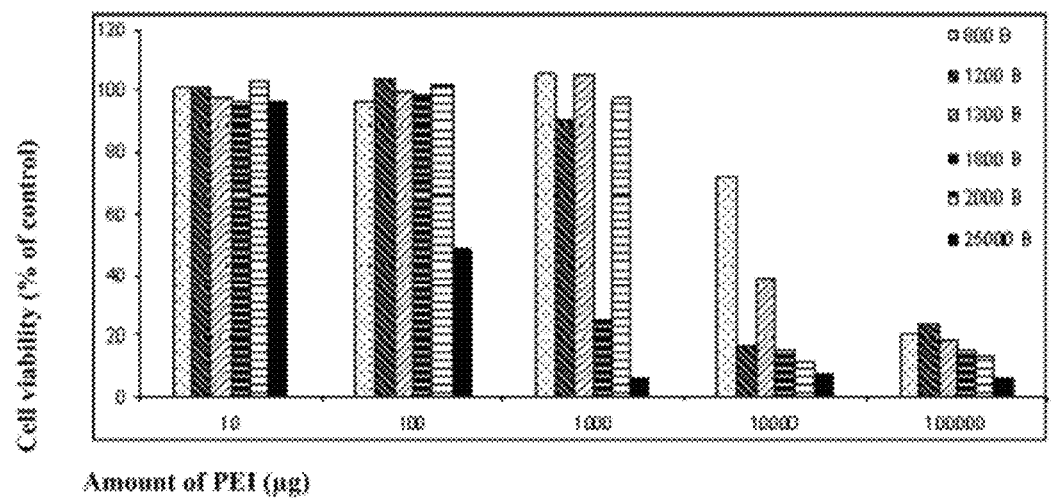
Figure 11:
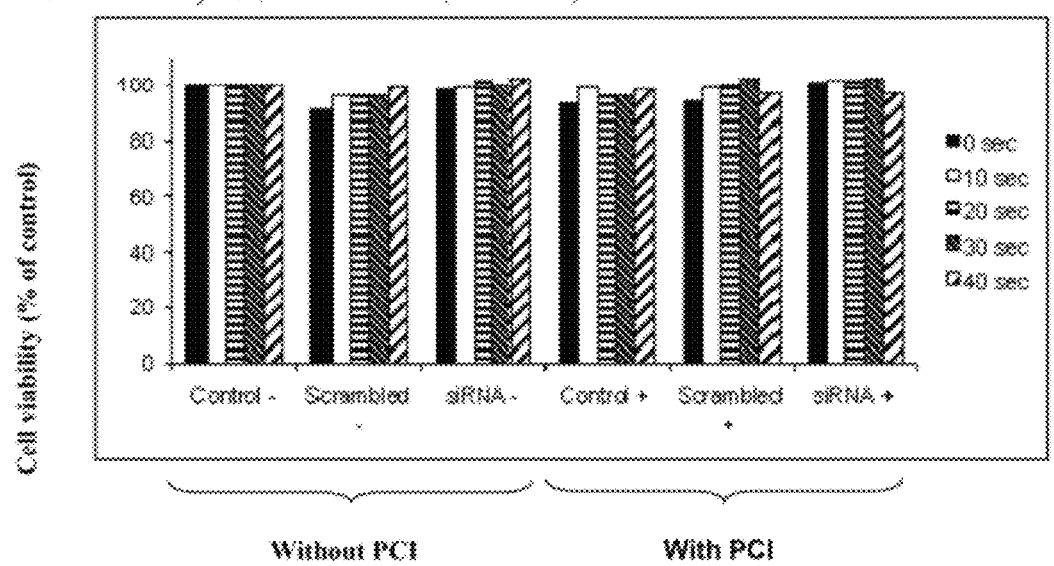

FIG. 11 shows the results of experiments to determine the toxicity of PEI alone and in combination with PCI and siRNA. The amounts of PEI and the light doses used in the PCI experiments are indicated. A. Toxicity of PEI without PCI. The MW of the different (branched) PEI carriers tested are indicated (mean of 5 individual experiments). B. Toxicity of the combination of PCI, PEI (1 µg) and siRNA at different light doses. The samples tested and the light doses used are shown. Control-=untreated control (with PEI but without PCI), Scrambled-=scrambled siRNA control (with PEI but without PCI), siRNA-=S100A4 siRNA (with PEI but without PCI). Control+, Scrambled+, and siRNA+ are the same as Control-, Scrambled-, and siRNA-, but with PCI (mean of 5 individual experiments).

Figure 12:
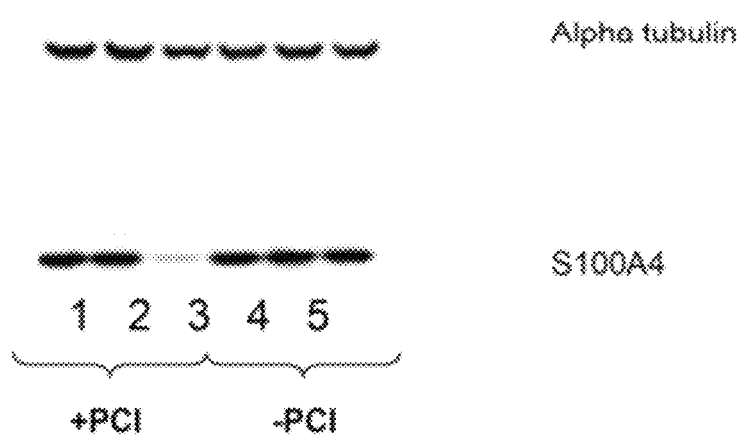

FIG. 12 shows PCI-induced delivery of siRNA molecules using Beta-Cyclodextrin amine as a carrier. Lanes 1 and 4=control without siRNA, lanes 2 and 5=control scrambled siRNA, lanes 3 and 6=S100A4 siRNA. The tubulin control band and the S100A4 band are as shown.

Figure 13:
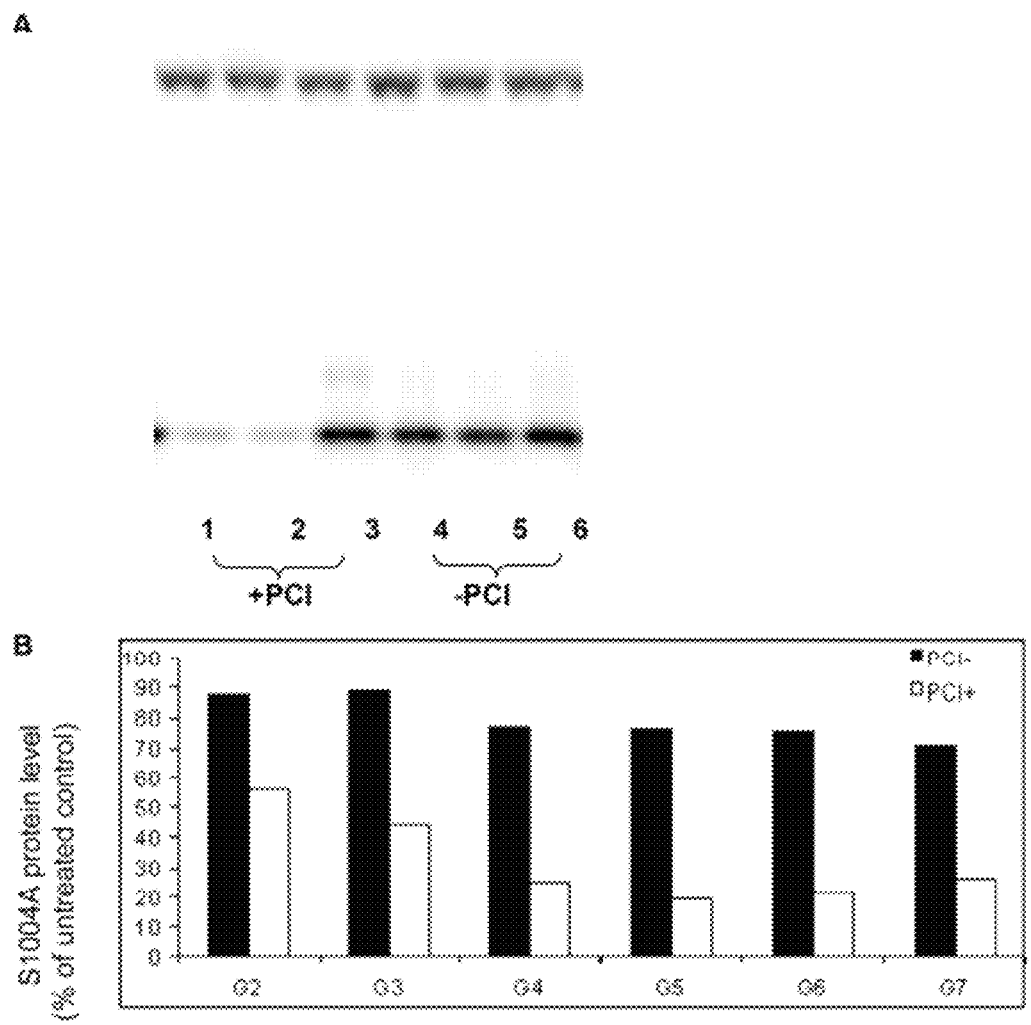

FIG. 13 shows PCI-induced delivery of siRNA molecules using poly amido amide (PAMAM) dendrimers (G2-7) with ethylenediamine core. (A) Western blot in which upper bands represent loading control (alpha tubulin), lower bands represent S100A4 levels. The samples in the different lanes are: 1. PAMAM G6 with PCI. 2. PAMAM G7 with PCI. 3. Control with PCI. 4. PAMAM G6 without PCI. 5. PAMAM 07 without PCI. 6. Control without PCI. (B). S100A4 protein level quantified by scanning of Western blots. Black bars represent transfections without PCI, while white bars represent transfection with PCI. The results are the mean of 3 individual experiments. The different forms of PAMAM used are indicated on the figure.

FIG. 14 shows the structural formula of G0, G1 and G2 PAMAM dendrimers.

Figure 15:
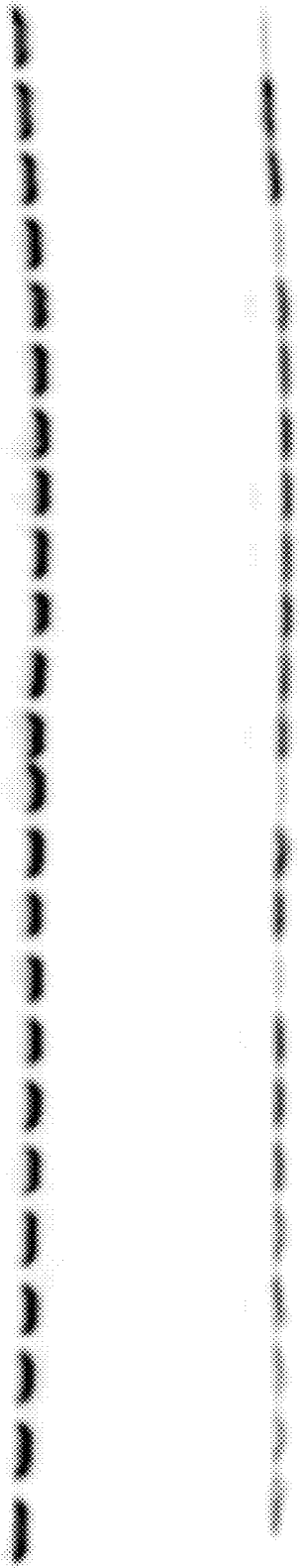

FIG. 15 shows the effect of PCI on polyarginine-mediated siRNA delivery. The level of S100A4 protein was analysed by Western blotting. The upper lane represent a loading control (alpha tubulin), the lower lane represent S100A4 levels. The samples on the gel were as follows: C+=control with PCI, S+=control scrambled siRNA with PCI, R+=S100A4 siRNA with PCI, C=control without PCI, S=control scrambled siRNA without PCI, R=S100A4 siRNA without PCI. 1=polyarginine MW 15,000-70,000 at 0.35 µg, 2=polyarginine MW 15,000-70,000 at 0.7 µg, 3=polyarginine MW>70.000 at 0.35 µg, 4=polyarginine MW>70,000 at 0.7 µg.

EXAMPLES

Materials and Methods

Cell Lines and Culture Conditions.

HCT-116 (colorectal adenocarcinoma) and SW620 (colorectal adenocarcinoma) were obtained from The American Type Culture Collection (Manassas, Va., USA). The OHS (osteosarcoma) and the RMS cell line was established at the Norwegian Radium Hospital. All cell lines were cultured using RPMI-1640 medium (Bio Whittaker, Verviers, Belgium or GibcoBRL, Paisley, UK), without antibiotics, but supplemented with 10% fetal calf serum (FCS; PAA Laboratories, Linz, Austria) and 2 mM L-glutamine (Bio Whittaker, Verviers, Belgium). Cells were grown and incubated at 37° C. in a humidified atmosphere containing 5% $CO_2$. All cell lines were tested and found negative for *Mycoplasma* infection prior to the experiments.

Light Source and Photosensitizer.

A Lumisource® (PCI Biotech AS, Oslo, Norway) was used as the light source. The Lumisource® is a bank of four fluorescent tubes designed to provide homogeneous illumination of the treatment area, emitting mainly blue light with a peak at 420 nm. The photosensitizer, disulfonated tetraphenylporphine ($TPPS_{2a}$) was purchased from Porphyrin Products (Logan, Utah, USA). $TPPS_{2a}$ was first dissolved in 0.1M NaOH, and thereafter diluted in phosphate-buffered saline (PBS), pH 7.5, to a concentration of 5 mg/ml and a final concentration of 0.002 M NaOH. The photosensitizer was light protected and stored at −20° C. until use.

siRNA Transfection without PCI.

Different transfection reagents for siRNA delivery were evaluated by using: Lipofectin™ Reagent from Life Technologies Inc. (Gaithersburg, Md., USA), Lipofectamine 2000 from Invitrogen (Carlsbad, Calif., USA), FuGene 6 from Roche Diagnostics (Mannheim, Germany), siPORT™ Lipid Transfection Agent from Ambion (Austin, Tex., USA), jetSI™ and jetSI™-ENDO from Polyplus transfection (Illkirch, France). All transfection reagents were handled according to the manufacturers' specifications. All cell lines were cultured as described in "Cell Lines and Culture Conditions", and cultivated for 24 hrs in 6-well plates to 50-70% confluence before transfection for 24, 48 or 96 hrs. Transfection reagent alone was applied to the cells as an untreated control, in addition to scrambled siRNA with transfection reagents.

The protocol used for jetSI/jetSI-ENDO was as follows for a standard 6 well plate:

Step 1: For each well, dilute 4.2(8.4) µl of jetSI/jetSI-ENDO solution into 100 µl of medium. Vortex vigorously (important: do not pipet to mix) and wait for 10 min (important: do not exceed 30 minutes).

Step 2: For each well, dilute 1.4 µg (100 nM) of siRNA duplex and into 100 µl of medium. Vortex gently.

Add the 100 µl jetSI medium solution to the 100 µl siRNA solution and mix solution at once (important: do not mix the solutions in the reverse order)

Immediately vortex-mix the solution for 10 seconds.

Incubate for 30 minutes at room temperature to allow complexes to form (important: do not exceed 1 hour).

During complex formation, remove the growth medium from the plates and add 0.8 ml of fresh serum containing medium (and photosensitizer, if used), pre-warmed at 37° C.

Add the 2000 jetSI/siRNA solution into each well and homogenize the mixture by gently swirling the plate.

Incubate the plate under the required cell culture conditions for 18 hrs, then wash the plate three times with fresh medium and re-incubate with 2-4 ml medium.

siRNA Transfection with PCI.

Cells were cultured and transfected as in "siRNA transfection without PCI", except for a few modifications. The photosensitizer $TPPS_{2a}$ (0.5 µg/ml) was added to the medium upon transfection. After 18 hrs of incubation, cells were washed 3 times with fresh medium, and incubated for 4 hrs before light treatment. After 4 hrs, cells were exposed to blue light (7 $mW/cm^2$) for different durations (60-90 see), depending on the cell line, and re-incubated for 24, 48 and 96 hrs before harvesting. To measure the PCI effect, effector siRNA, scrambled siRNA and transfection reagent alone were applied in the different wells of the same plate, with or without photosensitize; and given the same treatment. Cells were light protected by aluminium foil during these experiments.

Real-Time Reverse Transcriptase PCR of S100A4.

Total cellular RNA was isolated with the GenElute Mammalian Total RNA Miniprep Kit (Sigma-Aldrich, Steinheim, GER) and the iScript cDNA synthesis kit (BioRad, Hercules, Calif.) was used for reverse transcription. Both kits were used according to the manufacturers' manuals. All PCRs were run in parallels, real-time detection was obtained by use of SYBR Green I. For each PCR, 10 µl cDNA, 30 µl iQ SYBRGreen Supermix (BioRad), 300 nM of each primer and nuclease free water were added to a final volume of 60 µl. Samples of 25 each was then applied to the PCR plate. This method ensures that the parallels are true parallels, and that there is enough PCR mix for all replicates. Primer design was accomplished using the software Primer Express from Applied Biosystems (Applied Biosystems, Foster City, Calif.). The primer set used (forward primer 5'-AAGTTCAAGCTCAACAAGTCAGAAC-3 (SEQ ID NO:1) and reverse primer 5'-CATCTGTCCTTTTCCCCAAGA-3' (SEQ ID NO:2) amplifies a 79-bp segment in exon 2 and 3 of the S100A4 sequence.

Real-time reactions were run on an iCycler (Bio-Rad) with the following amplification protocol: 3 min initial denaturation at 95° C., 50 cycles of 10 s denaturation at 95° C., and 35 s annealing/extension at 60° C., one hold at 95° C. for 20 s followed by a hold for 1 min at 55° C., and finally a melt curve analysis of 80 steps each for 10 s, with 0.5° C. increase until a final temperature of 95° C. The quality of the RNA samples was verified by amplification of two housekeeping genes, TBP (forward primer 5'-GCCCGAAACGCCGAATAT-3' (SEQ ID NO:3) and reverse primer 5'-CGTGGCTCTCTTATCCTCATGA-3' (SEQ ID NO:4)) and RPLPO (forward primer 5'-CGCTGCTGAACATGCTCAAC-3' (SEQ ID NO:5) and reverse primer 5'-TCGAACACCTGCTGGATGAC-3' (SEQ ID NO:6)). The Gene Expression Macro, version 1.1 (Biorad), was used for the quantitative calculations. The program performs calculations based on the ΔΔ CT method, which allows comparison of cycle threshold values obtained using different sets of primers on the same set of samples.

Microscopy Studies.

Cells incubated with siRNA/jetSI-ENDO complexes as described (siRNA transfection with and without PCI) and analyzed with and without PCI treatment after 48 hrs with a Zeiss inverted microscope, Axiovert 200 equipped with filters for FITC (450-490 nm BP excitation filter, a 510 nm FT beamsplitter, and a 515-565 nm LP emission filter), and Rhodamine (546/12 nm BP excitation filter, a 580 nm FT beamsplitter, and a 590 nm LP emission filter) Pictures were composed by the use of Carl Zeiss AxioCam HR, Version 5.05.10 and AxioVision 3.1.2.1 software. Images were prepared with Adobe Photoshop 7.0 (Adobe, San Jose, Calif.) and Zeiss LSM Image Browser (Version 3).

Western Immunoblotting.

Protein lysates were prepared in 50 mM Tris-HCl (pH 7.5), containing 150 mM NaCl and 0.1% NP-40 with 2 g/ml pepstatin, aprotinin (Sigma Chemical Company, St Louis, Mo.) and leupeptin (Roche Diagnostics, Mannheim, Germany). Total protein lysate (30 µg) from each sample was separated by 12% SDS-polyacrylamide gel electrophoresis, and transferred onto Immobilon-P membranes (Millipore, Bedford, Mass.) according to the manufacturer's manual. As a loading and transfer control, the membranes were stained with 0.1% amidoblack. The membranes were subsequently incubated in 20 mM Tris-HCl (pH 7.5), containing 0.5 M NaCl and 0.25% Tween 20 (TBST) with 10% dry milk (blocking solution) before incubation with rabbit polyclonal anti S100A4 (diluted 1:300, DAKO, Glostrup, Denmark) and mouse monoclonal anti α-tubulin (diluted 1:250, Amersham Life Science, Buckinghamshire, England) in TBST containing 5% dry milk. After washing, the immunoreactive proteins were visualized using horseradish peroxidase conjugated secondary antibodies (diluted 1:5000 DAKO, Glostrup, Denmark), and the enhanced chemiluminescense system (Amersham Pharmacia Biotech, Buckinghamshire, England). S100A4 protein levels were reported as percentages of control sample and α-tubulin was used as a loading control.

Example 1 Gene Silencing in the OHS Cell Line

OHS cells were transfected with designed siRNAs to target the expression of the S100 A4 protein using various transfection systems. The standard transfection protocol was used in each case, according to the manufacturers' instructions. When photosensitiser was used, it was $TPPS_{2a}$ (0.5 µg in 1 ml transfection volume, apart from jetSI where a 2 ml transfection volume was used). The irradiation time in each case was 60 seconds.

20 µM siRNA stock solution was mixed with each different transfection reagents and transfected in 6-well plates to a final volume of 1 ml (except for jetSI and jetSI-ENDO, where the final volume was 2 ml).

siPORT Lipid=2 and 4 µl were tested, combined with 1.4 µg siRNA in 1000 µl

FuGene 6=4.2 µl and 8.4 µl were tested, combined with 1.4 µg siRNA in 1000 µl

Lipofectamine 2000=4.2 and 7 µl were tested, combined with 1.4 µg siRNA in 1000 µl Lipofectin=4.2 and 7 µl were tested, combined with 1.4 µg siRNA in 1000 µl jetSI=8.4 µl, combined with 2.8 µg siRNA in 2000 µl jetSI-ENDO=4.2 µl, combined with 1.4 µg siRNA in 2000

The siRNA molecule used was against the S100A4 mRNA sequence (GenBank accession number NM_002961). A specific siRNA having the sequence
5'-UGAGCAAGUUCAAUAAAGA-3' (SEQ ID NO:7)
3'-ACUCGUUCAAGUUAUUUCU-5' (SEQ ID NO:8)
was designed according to Elbashir et al., ((2001), Genes Dev. 15, 188-200). In addition to the siRNA designed against the selected target gene, control siRNA was designed by making a scrambled siRNA (5'-CG-CAUAAGUGAAAUAGAAU-3' (SEQ ID NO:9), 3'-GCGUAUUCAC UUUAUCUUA-5' (SEQ ID NO:10)) and a BLAST search was performed to eliminate false hybridisation. The GC content of the duplexes was kept within the 30-70% range, and all siRNA molecules were synthesized with dTdT overhangs at their 3' ends for optimal stability of the siRNA duplexes. siRNA molecules were ordered from Eurogentec (Seraing, Belgium).

Dried siRNA oligonucleotides were re-suspended to 100 µM in DEPC-treated water and stored at −20° C. Annealing was performed by separately aliquoting and diluting each RNA oligonucleotide to a concentration of 50 µM. Then, 30 µl of each RNA oligonucleotide solution and 15 µl of 5× annealing buffer were combined, to a final concentration of 50 mM Tris, pH 7.5, 100 mM NaCl in DEPC-treated water. The solution was then incubated for 3 min in a water bath at 95° C., followed by gradual cooling for 45 min on the workbench. Successful annealing was confirmed by 4% NuSieve agarose gel electrophoresis (data not shown).

It can be seen from FIG. 1 that PCI dependent gene silencing can be achieved through using the transfection agents jetSI and jetSI-ENDO. When these two transfection agents are used in the absence of PCI (i.e. irradiation, but in the absence of photosensitises), gene expression is around 75% of the control based on a measurement of protein levels using western blotting however when PCI is additionally used, gene expression is reduced to around 15% of the control.

In contrast, the use of SIPORT lipid or Fugene 6 as transfection agents did not achieve any significant reduction in gene expression, and the use of lipofectamine 2000 and lipofectin achieved inhibition of gene expression irrespective of whether PCI was also used.

Example 2 Gene Silencing in Different Cell Lines

Four different cell lines, HCT 116, SW620, OHS and RMS cells were transfected with 50 nM siRNA (jetSI-ENDO=4.2 µl, combined with 1.4 µg siRNA) designed to silence expression of S100A4 (see Example 1) using the standard jetSI-ENDO protocol, in the presence and absence of photosensitiser (0.5 µg/ml $TPPS_{2a}$). Cells were subjected to irradiation and S100A4 protein levels were determined by performing western blots 96 hours after irradiation (irradiation conditions were as follows, OHS=60 sec, SW620=80 sec, HCT116=90 sec, RMS=70 sec).

Examples of the results, are shown in FIG. 2B, and the results are represented graphically in FIG. 2A. In each cell type, the exposure of transfected cells to PCI treatment caused high levels of gene silencing, whereas those cells which were transfected with S100A4 siRNA but not subjected to PCI treatment showed significantly less gene silencing. The effect was shown to be specific since scrambled siRNA had no effect on gene expression, either in the presence or absence of PCI. There was no significant difference in the gene silencing effect between the different cell lines that were tested.

Example 3 Effect of siRNA Concentration and Time

The siRNA molecule designed to silence expression of the S100A4 protein was transfected into OHS cells at concentrations of 1 to 5 nM, using 4.2 µl jetSI-ENDO, and subjected to PCI treatment as described above.

Protein levels in cell lysates were measured using western blotting and are shown as a percentage of protein levels in untreated control cells in FIG. 3A.

The gene silencing effect increased with the concentration of siRNA to which the cells were exposed, although there is little difference between the silencing effects seen with 4 nM and 5 nM siRNA.

The scrambled siRNA molecule was also used in all experiments and was shown not to affect gene expression. As such, the gene inhibition effect is specific.

FIG. 2B shows the effect of time on gene silencing by altering the period of time between irradiation of the cells and harvesting of cell lysates for analysis. It can be seen that the longer the cells are left after irradiation and before harvesting, the more inhibition of gene expression is observed.

Example 4 Gene Silencing in OHS Cells after siRNA PCI Treatment

OHS cells were transfected with 100 nM siRNA or scrambled siRNA as described above and the effect of PCI treatment on protein and mRNA levels were determined 96 h after irradiation by western blotting and RT-PCR and compared to protein and mRNA levels in untreated controls.

The results shown in FIG. 4 indicate that, with respect to both protein and mRNA levels, large amounts of gene silencing of the S100A4 gene is observed when the siRNA specific for this gene is transfected with jetSI ENDO and the cells are subjected to PCI treatment (lane 5 of FIGS. 3A and B). A small amount of reduction in protein and RNA levels is seen without PCI treatment (lane 2 of FIGS. 3A and B), but this is markedly enhanced by the PCI treatment.

Example 5 Cytosolic Delivery of Labelled siRNA

OHS cells were transfected with 200 nM FITC labelled siRNA using jetSI ENDO ((jetSI-ENDO=8.4 µl, combined with 2.8 µg siRNA in a 1000 µl transfection volume=200 nM siRNA solution), with and without photosensitiser. Transfected cells were then subjected to irradiation.

The cells were inspected using phase contrast microscopy and fluorescence microscopy. By comparing the images, it was seen that in the absence of PCI treatment, the siRNA remains in a punctate distribution, which is representative of a distribution in endocytic vesicles (FIGS. 5a and c). There is also some leakage seen (right hand box in FIG. 5c). In contrast, following PCI treatment the labelled siRNA is seen to be distributed throughout the cytoplasm and in the nucleus (see FIG. 5b).

This demonstrates that PCI treatment is required for siRNA to be delivered to the required compartment of the cell, and that the delivery is dependent on PCI treatment.

Example 6 Gene Silencing Using siRNA-PCI Requires the Use of Less Carrier than Standard Transfection OHS cells were transfected with 100 nM siRNA using jetSI. In contrast to the experiments described above, jetSI was used at a lower concentration, i.e. at 50% of that recommended in the standard protocol. The standard protocol for a 6-well plate is: 2.8 µg siRNA+8.4 µl jetSI in 2000 µl medium, resulting in 100 nM siRNA in each well.

In contrast, for a 6-well plate, 1.4 µg siRNA was mixed with 4.2 µl jetSI in 1000 µl medium, resulting in 100 nM siRNA in each well. The total amount of complexes was thus reduced by 50%.

Following transfection, cells were either subjected to PCI treatment (the light dose for this experiment was 30 sec with 0.5 µg/ml TPPS2a) or left untreated, and gene silencing was measured using RT-PCR. The effector siRNA was able to reduce expression of the S100A4 gene to less than 20% of the untreated control, whereas little reduction was seen without PCI, and with the use of scrambled siRNA (either with or without PCI treatment).

This demonstrates that not only does the combined use of carriers with PCI offer the advantage of selective release of the siRNA molecule, but that high levels of gene silencing can be achieved using lower concentrations of the transfection agents, when combined with PCI. By comparison of FIG. 6 lane 5 with FIG. 1 lane 5 it can be seen that even using only 50% of the transfection agent that is used in Example 1, when PCI is also used, the degree of gene inhibition is much greater.

Example 7 Transfection Using PEI as Carrier

The siRNA target was selected against the S100A4 mRNA sequence (Gene Bank accession number NM_002961). siRNA 481-499 was used as effector (for sequence see Example 1).

Polyethylenimine (PEI) was evaluated for PCI-induced delivery. Cell lines were cultured (RPMI-1640 supplemented with 10% FBS, 10 ml L-glutamate, 10 ml Hepes) in 6-wells plates to 50-80% confluence before transfection. 100 nM siRNA was used as the standard concentration.

The PEI used was from Sigma and was diluted in sterile water and a stock solution containing 1000 µl PEI and 9000 µl sterile water was made. From the stock solution 1 and 10 µl was used to transfect of cells with 1.4 n siRNA (100 nM in each well).

PEI from Sigma was used (408719 Polyethylenimine (average Mw ~800 by LS, average Mn ~600 by GPC, branched, Low molecular weight, water-free)).

For the transfection, two solutions were made up, solution A, siRNA was diluted in 100 µl of serum free (OPTI-MEM I) medium. Solution B: PEI was diluted in 100 µl of serum free medium. Solutions A and B were mixed by gently mixing and incubated in room temperature for 30 min. The mixed solution was then added to the cells (1 ml of 100 nM siRNA).

PCI treatment was performed as described above for jetSI. Light doses for the PEI experiment was 40 sec. Protein levels were measured by Western blotting 96 hrs after irradiation.

It can be seen from FIG. 8 that S100A4 protein expression is reduced in the samples shown in lanes 5 and 6, i.e. the samples which have been subjected to transfection with PEI, and PCI treatment.

Example 8 Effect of PCI on siRNA Activity Using a 25 kDa PEI Carrier siRNA Transfection.

All cell lines were cultured as described in "Cell Lines and Culture Conditions", and plated in 6-well plates at 25-50% confluence before transfection. siRNA and carrier were complexed by gentle mixing and incubated for 30 min before being added to cells. Cells were transfected with siRNA, carrier, and either with or without photosensitiser (TPPS$_{2a}$=0.5 µg/ml) and incubated for 18 hrs, then washed 3 times with fresh medium and re-incubated for 4 hrs before light treatment. After 4 hrs, cells were exposed to blue light (7 mW/cm$^2$) for different durations (0-60 s), depending on the experiment, and re-incubated for 96 hrs before harvesting. To measure the effect of PCI upon gene silencing, specific siRNA, scrambled siRNA, and transfection reagent alone were applied in the different wells of the same plate, with or without photosensitiser, and given the exact same treatment. Cells were light protected by aluminum foil during the experiments.

siRNA mediated S100A4 gene silencing was measured at the protein level with and without PCI treatment using branched 25 kDa polyethylenimine (PEI) (1 µg/ml) and an siRNA targeting the S100A4 gene at a 100 nM concentration. The protocol described above was followed, using a light dose of 30 s, with both complexation and transfection in serum containing medium. FIG. 9A shows that with the use of PCI S100A4 siRNA typically reduced the S100A4 level down to 5-15% of the level in untreated controls (treated with PEI but without siRNA). In contrast, S100A4 siRNA without PCI was only able to reduce the S100A4 level down to 100-80% of the control. Untreated control levels were comparable to controls where a scrambled siRNA was used instead of the S100A4 specific siRNA (data not shown). In FIG. 9B, the experiment is represented by Western Blots. The upper bands represent a loading control (alpha tubulin) and the lower band represents S100A4 levels, as indicated on the figure. As can been seen from the blots, S100A4 is significant silenced with siRNA when using PCI, as compared to the situation for cells receiving S100A4 siRNA that were not treated with PCI, where no significant gene silencing could be detected.

Example 9 Effect of PCI on siRNA Activity with Different PEI Carriers Used at Different Concentrations PCI effects on of S100A4 siRNA activity was investigated for using various branched PEI-formulations at different concentrations (0.1 µg/ml, 1 µg/ml, 10 µg/ml and 100 µg/ml, 1 ml medium was used per well). The PEI species tested (all branched) were as follows:

| PEI | MW (Da) |
|---|---|
| 1 | 800 |
| 2 | 1200 |
| 3 | 1300 |
| 4 | 1800 |
| 5 | 2000 |
| 6 | 25000 |

The protocol described in Materials and Methods was followed, using a light dose of 30 s, with both complexation and transfection in serum containing medium. The siRNA was used at a concentration of 100 nM. As can be seen from FIG. 10 the use of PCI can significantly enhance the gene silencing effect of the S100A4 siRNA with different PEI carriers. This effect is especially prominent with lower amounts of PEI (1 and 10 µg/ml) where the effect without PCI was very modest, except for PEI 4 (MW 1800) at 10 µg/ml. At these two PEI concentrations PCI significantly enhanced the gene silencing effect of all the tested PEI species, except for PEI 1 (MW 800).

Without PCI the degree of gene silencing increases with increasing PEI concentration, with PCI this effect is not so pronounced, except that no gene silencing (neither with nor without PCI) can be observed with 0.1 µg/ml PEI. One possible explanation for this is that this amount of PEI is not high enough to complex all the siRNA, leading to negatively charged complexes that are not taken up by the cells. Without PCI there seems to be a trend towards increased gene silencing with increasing molecular weight of the PEI carrier; with PCI this effect is not so conspicuous, again with exception of PEI 1 (MW 800). The effect of PEI without PCI at higher MWs and higher amounts is probably due to the reported endosomolytic properties of PEI working only at high concentrations of PEI.

This shows that PCI can substitute this effect making it possible to use low amounts and low MWs of polyethylenimine, a property that is very advantageous to avoid toxicity and other concerns with PEI carriers.

Example 10 Toxicity Studies

The toxicity of different PEI formulations (MW 800-25.000) alone (without PCI treatment) was first assessed. In this assay, OHS cells were plated in 96-well plates and allowed to adhere overnight in serum containing medium. The medium was then discarded, and cells were incubated with medium and various PEI formulations under different concentrations for 20 hrs. The PEI containing medium was then discarded, and MTS solution (from Promega, Madison, Wis., USA) was added to each well (1:6 dilution, 100 µl/well), and plates were re-incubated for another 4 hrs. Absorbance at 490 nm was measured.

As can be observed from FIG. 11A, toxicity increased with increasing molecular weight of the PEI formulation (e.g. 25000 PEI vs. 800 PEI) and with increasing amounts of PEI. Importantly, PEI formulations at 1 µg/ml (not shown) and 10 µg/ml did not show significant toxicity. For these samples, a significant biological effect of the siRNA could be achieved with PCI, while the effect without PCI was very modest (see Example 9).

The toxicity of PEI with siRNA/PCI treatment was also assessed. OHS cells were plated in 6-well plates and allowed to adhere overnight in serum containing medium. The medium was then discarded, and cells in 6-well plates were transfected with PEI alone, scrambled siRNA and specific siRNA, with or without photosensitiser. Cells were then incubated overnight and subsequently washed and treated with blue light (PCI) as described in "siRNA transfection". After re-incubation for 44 hrs, 166.6 µl MTS solution) was added to each well and, plates were re-incubated for another 4 hrs. Absorbance at 490 nm was measured. FIG. 11B shows the toxicity of the combined treatment with PEI (MW 25 000) at 1 µg/ml, 100 nM siRNA and PCI at different light-doses. As can be seen from the graph, the PCI treatment did not induce significant toxicity at the light-dose used (30 s) in all the PET gene silencing experiments, which is a light-dose at which a strong gene silencing effect was induced by PCI (see FIG. 10). Even at the higher light dose of 40 s no cytotoxicity of the PCI treatment could be observed, showing that PCI can induce fully enhance siRNA delivery without giving cytotoxic effects.

Example 11 PCI-Induced Delivery of siRNA Molecules Using β-Cyclodextrin Amine as a Carrier The effect of PCI on Beta-cyclodextrin amine mediated siRNA delivery was investigated. A light-dose of 60 s was used in these experiments, and the protocol described in Materials and Methods was followed. Beta-cyclodextrin amine as described above with n=6 and X=4 was diluted in sterile water and complexation and transfections were performed in serum-free medium. As can been seen from the Western blot (FIG. 12) Beta-cyclodextrin amine at 100 µg/ml (1 ml was used per well) complexed with 50 nM (0.7 µg) siRNA was effective for PCI induced siRNA delivery (lane 3), while under these conditions delivery without PCI was ineffective (lane 6). The Beta-cyclodextrin amine used in this study consists of Beta-cyclodextrin molecules conjugated through an amine bridge responsible for binding to siRNA, and is described in Hwang S. J. et al. (2001, Bioconjugate Chem. 12, 280-290).

Example 12 PCI-Induced Delivery of siRNA Molecules Using Poly Amido Amide (PAMAM) Dendrimers (G2-7) with Ethylenediamine Core Poly amido amide (PAMAM) dendrimers were evaluated for PCI-induced siRNA delivery. PAMAM was diluted in sterile water and transfections were performed in serum containing medium. Different types of PAMAM dendrimers (G2-7) at 100 µg/ml (1 ml was used per well) were complexed with 100 nM (1.4 µg) siRNA and transfection was carried out according to the procedures described above. A light-dose of 30 s was used in these experiments. As can be seen from the Western blot (FIG. 13A) PCI could strongly enhance the activity of siRNA (lanes 1 and 2) under conditions where siRNA/PAMAM alone was ineffective for gene silencing (lanes 4 and 5). As can be seen in FIG. 13B this effect was apparent also for several other types of PAMAM dendrimers, indicating that PCI can generally enhance siRNA delivery by polyamine-based dendrimers.

The different types of PAMAM used in the study containing different amounts of surface amine groups are as follows:

G2=Molecular Formula: $[NH_2(CH_2)_2NH_2]:(G=2)$; dendri PAMAM$(NH_2)_{16}$

G3=Molecular Formula: $[NH_2(CH_2)_2NH_2]:(G=3)$; dendri PAMAM$(NH_2)_{32}$

G4=Molecular Formula: $[NH_2(CH_2)_2NH_2]:(G=4)$; dendri PAMAM$(NH_2)_{64}$

G5=Molecular Formula: $[NH_2(CH_2)_2NH_2]:(G=5)$; dendri PAMAM$(NH_2)_{128}$

G6=Molecular Formula: $[NH_2(CH_2)_2NH_2]:(G=6)$; dendri PAMAM$(NH_2)_{256}$

G7=Molecular Formula: $[NH_2(CH_2)_2NH_2]:(G=7)$; dendri PAMAM$(NH_2)_{512}$

| Generation (G) | MW | Measured diameter (nm) | Surface amine groups |
|---|---|---|---|
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |

Example 13 PCI-Induced Delivery of siRNA Using Poly-L-Arginine Hydrochloride as the Carrier Polyarginine was diluted in sterile water and transfections were performed in serum free medium. Two types of polyarginine carriers (molecular weight of 15000-70000 and >70000) were tested. Polyarginine at 0.35 or 0.7 µg/ml (1 ml was used per well) were complexed with 100 nM (1.4 µg) siRNA, and the protocol described above was followed, assessing S1004A expression by Wester blotting after giving a light-dose of 30 s. As can be seen from FIG. 15, there is a significant difference in gene silencing efficacy between PCI-treated and non-treated samples. Thus, while all the PCI-treated samples (R+-samples in FIG. 15) shows significant gene silencing, no silencing effect can be observed in corresponding samples not treated by PCI (R-samples in FIG. 15). Thus, PCI is effective in inducing gene silencing with both the different polyarginine carriers tested and at both the concentrations used, showing that PCI can significantly enhance siRNA delivery by a cationic peptide-based carrier.

The invention claimed is:

1. A method for introducing an siRNA molecule into the cytosol of a cell, said method comprising
   i) contacting said cell with an siRNA molecule, a carrier and a photosensitizing agent; and
   ii) irradiating the cell with light of a wavelength effective to activate the photosensitizing agent,
   wherein said carrier comprises a cationic polyamine selected from
      (a) a branched polyethyleneimine (PEI) with a molecular weight of from 1.2 to 1.8 kDa, wherein the N/P ratio of the siRNA and PEI used in said method is from 5 to 300, and wherein said PEI has an $M_n$ (number average molecular weight) value of 500-1500 by gel permeation chromatography (GPC), and
      (b) a cationic peptide selected from poly-Arginine and a copolymer of L or D arginine, wherein said cationic peptide is at least 70,000 Da in molecular weight.

2. The method of claim 1 wherein the siRNA molecule is 12-28 nucleotides long.

3. The method of claim 1 wherein said cell is a mammalian cell.

4. The method of claim 1, further comprising the additional step of contacting said siRNA with said carrier.

5. The method of claim 1 wherein the siRNA molecule and the carrier molecule are contacted with one another for 20-40 minutes before being contacted with the cell.

6. The method of claim 1, wherein 10 nM-200 nM siRNA is used for transfection.

7. The method of claim 1 wherein a photosensitizer carrier selected from a polycation, polyethyleneimine, a dendrimer, a cationic lipid and a peptide is additionally present.

8. The method of claim 1, wherein the siRNA is mixed with the carrier so as to form a complex, which is then administered to the cell simultaneously or sequentially with the photosensitizing agent.

9. The method of claim 1 wherein said method is performed by contacting said cell with a photosensitizing agent, contacting said cell with the carrier and the siRNA molecule to be introduced and irradiating said cell with light of a wavelength effective to activate the photosensitizing agent, wherein said irradiation is performed prior to the cellular uptake of said siRNA molecule and said carrier into an intracellular compartment containing said photosensitizing agent.

10. A method of inhibiting the expression of a target gene comprising introducing an siRNA molecule into a cell containing said target gene by the method of claim 1, wherein said siRNA molecule specifically inhibits expression of said target gene.

11. A method of treating or preventing a disease, disorder or infection in a patient comprising introducing an siRNA molecule and carrier into one or more cells in vitro, in vivo or ex vivo according to the method of claim 1 and where necessary administering said cells to said patient.

12. The method of claim 11 wherein the disease to be treated is typified by abnormal gene expression or which would benefit from suppression of one or more genes.

13. The method of claim 11 wherein the siRNA is mixed with the carrier so as to form a complex, which complex is then introduced to the one or more cells simultaneously with the photosensitizing agent.

14. The method of claim 11 wherein the siRNA is mixed with the carrier so as to form a complex, which complex is then introduced to the one or more cells sequentially with the photosensitizing agent.

15. The method of claim 12, wherein the disease is cancer.

16. The method of claim 1 wherein the photosensitizing agent is selected from a porphyrin, phthalocyanine, purpurin, chlorin, benzoporphyrin, lysomotropic weak base, naphthalocyanine, cationic dye, tetracycline, 5-aminolevulinic acid or an ester thereof, or a derivative or a pharmaceutically acceptable salt of any said photosensitizing agent.

17. The method of claim 16 wherein the photosensitizing agent is sulfonated tetraphenylporphine (TPPS) $TPPS_4$, $TPPS_{2a}$, tetrasulfonated aluminium phthalocyanine (AL-PcS) $AlPcS_{2a}$, sulfonated meso-tetraphenyl chlorin (TPCS) $TPCS_{2a}$, 5-aminolevulinic acid or an ester or pharmaceutically acceptable salt thereof.

18. A combination of (a) a photosensitizing agent and (b) a composition that comprises an siRNA molecule and a carrier molecule wherein the carrier molecule comprises a cationic polyamine selected from (i) a branched polyethyleneimine (PEI) with a molecular weight of from 1.2 to 1.8 kDa, wherein the N/P ratio of the siRNA and PEI in said composition is from 5 to 300, and wherein said PEI has an $M_n$ (number average molecular weight) value of 500-1500 by gel permeation chromatography (GPC), and (ii) a cationic peptide selected from poly-Arginine and a copolymer of L or D arginine, wherein said cationic peptide is at least 70,000 Da in molecular weight.

19. The combination of claim 18 wherein the composition and the photosensitizing agent are formulated for simultaneous, separate, or sequential use in therapy.

* * * * *